(12) United States Patent
Smith et al.

(10) Patent No.: US 7,439,319 B2
(45) Date of Patent: Oct. 21, 2008

(54) SELECTIVE SUBSTRATES FOR MATRIX METALLOPROTEINASES

(75) Inventors: Jeffrey W. Smith, San Diego, CA (US); Emily I. Chen, Encinitas, CA (US); Steven J. Kridel, Clemmons, NC (US)

(73) Assignee: Burnham Institute for Medical Research, La Jolla, CA (US)

( * ) Notice: Subject to any disclaimer, the term of this patent is extended or adjusted under 35 U.S.C. 154(b) by 141 days.

(21) Appl. No.: 10/243,613

(22) Filed: Sep. 13, 2002

(65) Prior Publication Data

US 2004/0053823 A1  Mar. 18, 2004
US 2005/0181989 A9  Aug. 18, 2005

Related U.S. Application Data

(60) Provisional application No. 60/421,149, filed on Sep. 14, 2001.

(51) Int. Cl.
*A61K 38/00* (2006.01)
*C07K 16/00* (2006.01)

(52) U.S. Cl. ............... 530/300; 530/328; 530/329; 530/333

(58) Field of Classification Search ............ 530/300
See application file for complete search history.

(56) References Cited

U.S. PATENT DOCUMENTS 5,518,912 A * 5/1996 Zasloff et al. ............ 435/226
6,399,075 B1 * 6/2002 Howley et al.

OTHER PUBLICATIONS

Burgess et al., J of Cell Bio. 111:2129-2138, 1990.*
Lazar et al., Molecular and Cellular Biology 8:1247-1252, 1988.*
Bowie et al., Science, 247:1306-1310, 1990.*
PIR Database, Accession No. S54424, Apr. 1997.*
PIR Database, Accession No. A45185, Sep. 1993.*
PIR Database, Accession No. D71810, Feb. 12, 1999.*
Simth et al., Chem Rev, vol. 97, p. 391-410.*
Jain, Scientific American Jul. 1994.*
Gura, Science, v278, 1997, pp. 1041-1042.*
Simth et al., Chem Rev, vol. 97 p. 391-410, 1997.*
Bergers et al., "Matrix metalloproteinase-9 triggers the angiogenic switch during carcinogenesis," *Nature Cell Biol.* 2:737-744 (2000).
Birkendal-Hansen, "Proteolytic remodeling of extracellular matrix," *Curr. Opin. Cell Biol.* 7:728-735 (1995).
*Burger's Medicinal Chemistry and Drug Discovery* Editor Manfred E. Wolff, Ch. 15, pp. 619-620, John Wiley & Sons Inc., New York, New York (1995).
Chen et al., "A Unique Substrate Recognition Profile for Matrix Metalloproteinase-2," *J. Biol. Chem.* 277:4485-4491 (2002).
Coussens et al., "MMP-9 Supplied by Bone Marrow-Derived Cells Contributes to Skin Carcinogenesis," *Cell* 103:481-490 (2000).

DeFeo-Jones et al., "A peptide-doxorubicin 'prodrug' activated by prostate-specific antigen selectively kills prostate tumor cells positive for prostate-specific antigen in vivo," *Nature Med.* 6:1248-1252 (2000).
Deng et al., "Substrate Specificity of Human Collagenase 3 Assessed Using a Phage-displayed Peptide Library," *J. Biol. Chem.* 275:31422-31427 (2000).
Denmeade et al., "Enzymatic Activation of Doxorubicin-Peptide Prodrug by Prostate-Specific Antigen," *Cancer Res.* 58:2537-2540 (1998).
Folkman, "Angiogenesis in cancer, vascular, rheumatoid and other disease," *Nature Med.* 1:27-31 (1995).
Goldman et al., "Targeted Gene Delivery to Kaposi's Sarcoma Cells via the Fibroblast Growth Factor Receptor," *Cancer Res.* 57:1447-1451 (1997).
Koivunen et al., "Tumor targeting with a selective gelatinase inhibitor," *Nature Biotech.* 17:768-774 (1999).
Kridel et al., "Substrate Hydrolosis by Matrix Metalloproteinase-9," *J. Biol. Chem.* 276:20572-20578 (2001).
Kridel et al., "A Substrate Phage Enzyme-Linked Immunosorbent Assay to Profile Panels of Proteases," *Anal. Biochem.* 294:176-184 (2001).
Murphy and Crabbe, "Gelatinases A and B," *Methods Enzymol.* 248:470-484 (1995).
NCBI Accession No. P28618 (Dec. 1992).
Netzel-Arnett et al., "Comparative Sequence Specificities of Human 72- and 92-kDa Gelatinases (Type IV Collagenases) and PUMP (Matrilysin)," *Biochemistry* 32:6427-6432 (1993).
Netzel-Arnett et al., "Sequence Specificities of Human Fibroblast and Neutrophil Collagenases," *J. Biol. Chem.* 266:6747-6755 (1991).
Ohkubo et al., "Identification of Substrate Sequences for Membrane Type-1 Matrix Metalloproteinase Using Bacteriophage Peptide Display Library," *Biochem. Biophys. Res. Comm.* 266:308-313 (1999).

(Continued)

*Primary Examiner*—Larry R. Helms
*Assistant Examiner*—Lei Yao
(74) *Attorney, Agent, or Firm*—McDermott Will & Emery LLP

(57) ABSTRACT

The invention provides isolated MMP-2, MMP-9 and MT1-MMP selective substrate polypeptides or functional peptidomimetics. The selective substrate polypeptides contain the following sequences: MMP-2 selective substrate polypeptides contain SEQ ID NOS:1-27, MMP-9 selective substrate polypeptides contain SEQ ID NOS:28-35, and MT1-MMP selective substrate polypeptide contain SEQ ID NOS:36-40. In addition, the invention provides a method of preferentially directing a moiety to a site of MMP-2 activity by administering to a subject an effective amount of an isolated MMP-2 selective substrate polypeptide containing SEQ ID NOS:45-47 linked to a moiety. Also provided is a method of preferentially directing a moiety to a site of MMP-9 activity by administering to a subject an effective amount of an isolated MMP-9 selective substrate polypeptide containing SEQ ID NO:44 linked to a moiety, and preferentially directing a moiety to a site of MT1-MMP activity by administering to a subject an effective amount of an isolated MT1-MMP selective substrate polypeptide containing SEQ ID NOS:36-40 linked to a moiety.

38 Claims, 4 Drawing Sheets

OTHER PUBLICATIONS

Ohuchi et al., "Membrane Type 1 Matrix Metalloproteinase Digests Interstitial Collagens and Other Extracellular Matrix Macromolecules," *J. Biol. Chem.* 272:2446-2451 (1997).

Rak et al., "Consequences of angiogenesis for tumor progression, metastasis and cancer therapy," *Anti-Cancer Drugs* 6:3-18 (1995).

Schechter and Berger, "On the Size of the Active Site in Proteases. I. Papain," *Biochem. and Biophys. Res. Comm.* 27:157-162 (1967).

Smith et al., "Rapid Identification of Highly Active and Selective Substrates for Stromelysin and Matrilysin Using Bacteriophage Peptide Display Libraries," *J. Biol. Chem.* 270:6440-6449 (1995).

Smith et al., "Building Synthetic Antibodies as Adhesive Ligands for Integrins," *J. Biol. Chem.* 269:32788-32795 (1994).

Weissleder et al., "In vivo imaging of tumors with protease-activated near-infrared fluorescent probes," *Nature Biotech.* 17:375-378 (1999).

* cited by examiner

US 7,439,319 B2

SELECTIVE SUBSTRATES FOR MATRIX METALLOPROTEINASES

This application is based on, and claims the benefit of, U.S. Provisional Application No. 60/421,149, filed Sep. 14, 2001, which was converted from U.S. Ser. No. 09/953,592, and which is incorporated herein by reference.

This invention was made with government support under grant numbers CA 69036 and AR 42750 awarded by the National Institutes of Health. The United States Government has certain rights in this invention.

BACKGROUND OF THE INVENTION

This invention relates generally to the fields of biochemistry and molecular medicine, and more specifically to polypeptide substrates for matrix metalloproteinases.

Proteinases are a class of enzymes that are involved in the cleavage or hydrolysis of a variety of proteins. Matrix metalloproteinases (MMPs) are a family of structurally related proteinases that have been implicated in the hydrolysis of several proteins, including proteins involved in blood vessel formation (angiogenesis) and proteins that make up the extracellular matrix (ECM). These proteinases are mediators of both normal and pathological processes in the body. For example, matrix metalloproteinases are involved in normal tissue remodeling, such as wound healing, and normal angiogenesis, such as occurs in the female reproductive cycle. However, these proteinases are also involved in pathological processes such as angiogenesis within tumors and tumor metastasis.

Several matrix metalloproteinases have been implicated in tumor invasion. For example, membrane type-I matrix metalloproteinase (MT1-MMP) is expressed in various tumors. This metalloproteinase is known to hydrolyze many types of ECM proteins such as interstitial collagens, gelatin and proteoglycan. In addition, MT1-MMP is an activator of another matrix metalloproteinase, MMP-2. MMP-2 (also called gelatinase A) is also expressed in various tumors and, when activated, can play a role in metastatic processes. When MMP-2 activity is reduced, as seen in genetically engineered mice that lack the MMP-2 gene, tumor angiogenesis is also reduced. A third matrix metalloproteinase of interest in tumorigensis is MMP-9 (also called gelatinase B). This metalloproteinase is reported to be part of the "angiogenic switch" that initiates the vascularization of tumors. Solid tumors require vascularization for growth and so this matrix metalloproteinase, as well as other matrix metalloproteinases, has been a target for designing drugs to inhibit matrix metalloproteinase function and tumor angiogenesis. However, many of these drugs are broad spectrum metalloproteinase inhibitors and exhibit unwanted side effects.

Since matrix metalloproteinases are overexpressed at sites of disease they represent an opportunity for designing new therapeutic and diagnostic agents. In the case of therapeutic agents, there is a need for methods of targeting biologically active compounds to the site of MMP action. Such targeting can increase the efficacy of these compounds while reducing their unwanted side effects. Several groups have put forth strategies in which a compound can be targeted to a desired site of action by linking it to a binding molecule that binds selectively at a desired site. However, binding molecules with sufficient affinity and selectivity are not always available, particularly for the MMPs. The present invention overcomes this problem by providing polypeptides that are selective MMP substrates. In the case of diagnostic agents, there is a need to be able to measure MMP activity, both in vitro and in vivo. Most current approaches measure MMP expression level; however, because the MMPs are regulated post-translationally, protein expression levels do not indicate protease activity. The present invention provides selective MMP substrate polypeptides that are cleaved by catalytically active MMPs and so these polypeptides can be used to quantify MMP activity for diagnostic uses.

Thus, there exists a need to identify selective substrates that can target a specific active matrix metalloproteinase for use as diagnostics and therapeutics. The present invention satisfies this need and provides related advantages as well.

SUMMARY OF THE INVENTION

The invention provides isolated MMP-2, MMP-9 and MT1-MMP selective substrate polypeptides or functional peptidomimetics. The selective substrate polypeptides contain the following sequences: MMP-2 selective substrate polypeptides contain SEQ ID NOS:1-27, MMP-9 selective substrate polypeptides contain SEQ ID NOS:28-35, and MT1-MMP selective substrate polypeptide contain SEQ ID NOS:36-40. In addition, the invention provides a method of preferentially directing a moiety to a site of MMP-2 activity by administering to a subject an effective amount of an isolated MMP-2 selective substrate polypeptide containing SEQ ID NOS:45-47 linked to a moiety. Also provided is a method of preferentially directing a moiety to a site of MMP-9 activity by administering to a subject an effective amount of an isolated MMP-9 selective substrate polypeptide containing SEQ ID NO:44 linked to a moiety, and preferentially directing a moiety to a site of MT1-MMP activity by administering to a subject an effective amount of an isolated MT1-MMP selective substrate polypeptide containing SEQ ID NOS:36-40 linked to a moiety.

DETAILED DESCRIPTION OF THE INVENTION

Figure 1:
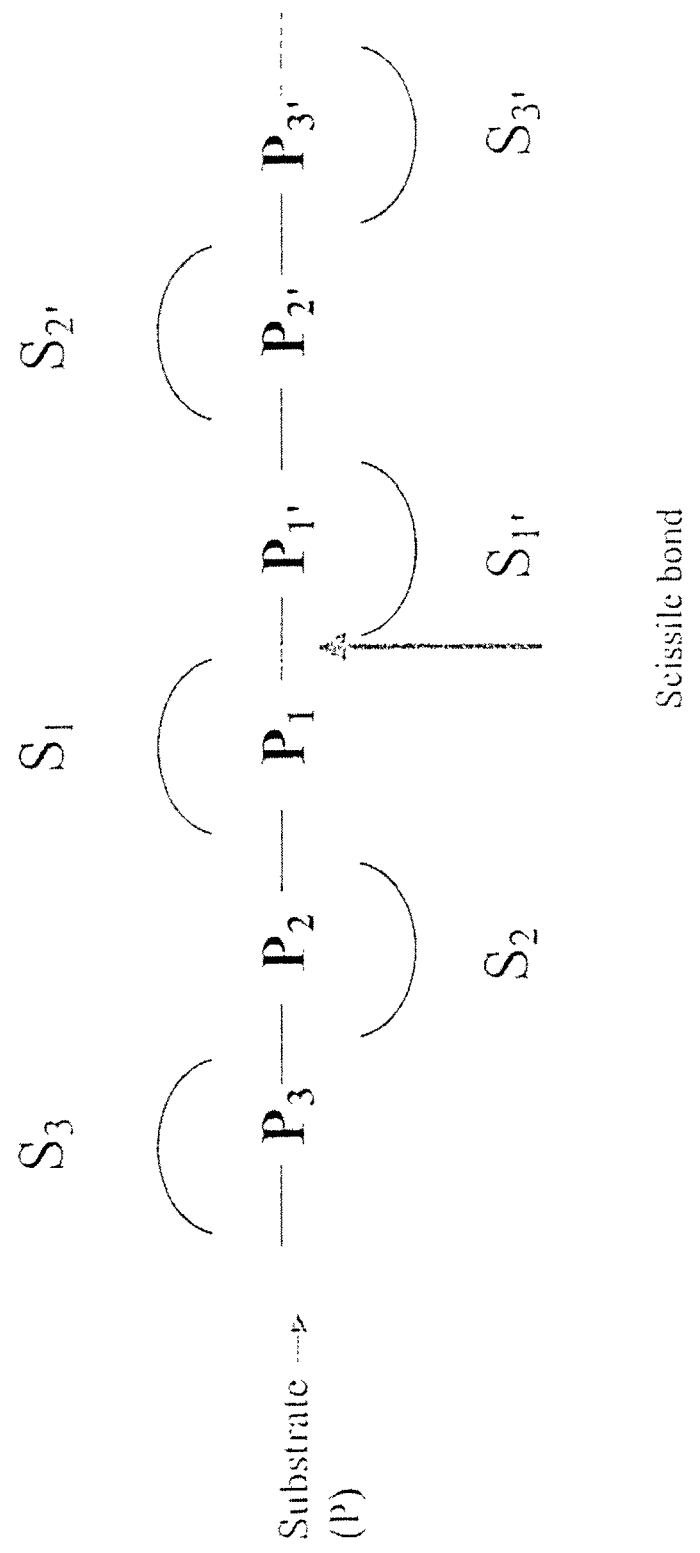
FIG. 1 illustrates the nomenclature developed by Schecter and Berger to describe positions within a proteinase substrate (Schecter and Berger, *Biochem. and Biophys. Res. Comm.* 27:157-162 (1967)). Individual subsites within the active site of a proteinase are denoted as "S" and the corresponding positions within the substrate are denoted as "P". The hydrolyzed or scissile bond within the substrate falls between the $P_1$ and $P_{1'}$ residue. Positions on the amino-terminal side of the scissile bond are called "unprimed" whereas positions on the carboxy-terminal side are called "primed."

The present invention provides isolated MT1-MMP, MMP-2, or MMP-9 selective substrate polypeptides, or functional peptidomimetics thereof. In addition, these polypeptides of the invention, or peptidomimetics thereof, can be linked to a moiety such as a diagnostic moiety or a therapeutic moiety.

The invention also provides methods of preferentially directing a moiety to a site of MT1-MMP, MMP-2, or MMP-9 activity by administering to a subject an isolated MT1-MMP, MMP-2, or MMP-9 selective substrate polypeptide linked to a moiety. The methods of the invention can be useful in diagnosing or treating diseases where these metalloproteinases are involved which include, for example, cancer or other disorders involving pathogenic angiogenesis. Disorders involving pathogenic angiogenesis include, for example, diseases of ocular neovacularization, arthritis, atherosclerosis, endometriosis, and skin diseases.

Substrates selective for a particular MMP are advantageous for several reasons. A selective substrate of the invention can be linked to a diagnostic agent, including an imaging agent, to determine whether an active MMP is expressed at a particular site. For example, selective substrates of the invention can be used to distinguish the identity of an active MMP from another related MMP. Other methods for identifying MMPs, including detection of MMP mRNA or MMP protein levels, are not designed to assess the activity level of the MMP. Distinguishing one MMP from another MMP is advantageous because a particular site, such as a tumor, can express several different MMPs that are related to each other. The selective substrates of the invention have the added advantage of detecting which of the MMPs are active at a particular site in a particular disease state or at a particular time during the development of the disease or during treatment. In this way the profile of active MMPs at a site such as a tumor can be characterized. A particular active MMP, for example, can be diagnostic of a specific stage of a tumor or can be correlated to a particular prognosis for the patient or can indicate a particular course of treatment. In addition, an active MMP in a particular disease can be targeted for the design of pharmaceuticals to alter the activity of that MMP.

The selective substrates of the invention can also be used in the treatment of MMP-associated diseases. The selective substrates of the invention can be linked to a therapeutic moiety thus preferentially directing the moiety to a site of activity for that particular MMP. The selective substrates of the invention target active MMPs which can be more relevant in the course of a disease than other MMPs. Targeting a particular active MMP, without targeting other MMPs, can result in less side effects and in greater concentration of the therapeutic moiety at the desired location.

Another advantage of the selective substrate polypeptides of the invention is that they can target MMPs even if the substrate polypeptide binds the MMP with low affinity. Selective substrate polypeptides with low affinity for the active site of a MMP can be useful in the invention for targeting a moiety provided the rate of hydrolysis of the polypeptide is high. The use of lower affinity binding polypeptides is possible because the substrate polypeptides of the invention can have utility as targeting agents because of the product of two parameters, binding affinity and the rate of hydrolysis.

MMP-2 selective substrate polypeptides useful in the invention include, for example, polypeptides containing the amino acid sequences disclosed in SEQ ID NOS:1-27, 41, 42, 43, 45, 46, and 47. In one embodiment, polypeptides containing the amino acid sequences disclosed in SEQ ID NOS:1-27 are useful in the invention. A polypeptide of the invention can have, for example, up to 10, 20, 40, 100 or more residues. In another embodiment, MMP-2 selective substrate polypeptides, or peptidomimetics thereof, linked to a moiety can be administered to a subject to preferentially direct the moiety to a site of MMP-2 activity. The site can be, for example, in vivo, in situ, or in vitro.

The methods of the invention are useful for preferentially directing a variety of moieties to a site of MT1-MMP, MMP-2, or MMP-9 activity. Moieties including diagnostic moieties and therapeutic moieties are useful in the invention. Such a moiety can be, for example, an imaging moiety including a radionucleotide or a quenched fluorophore. In addition, such a moiety can be a therapeutic moiety such as a cytotoxic agent; a chemotherapeutic agent such as an anthracyclin, alkylating agent, vinca alkaloid, nucleotide analog, cis-platinum, doxorubicin, methotrexate or mitomycin C; or a pro-apoptotic peptide such as $_D$(KLAKLAK)$_2$. A therapeutic moiety useful in the invention also can be an anti-angiogenic polypeptide such as thrombospondin, angiostatin, endostatin, pigment epithelium-derived factor, or active antithrombin. A therapeutic moiety useful in the invention further can be a pro-angiogenic agent such as vascular endothelial growth factor, fibroblast growth factor, or an agent that promotes tissue repair. In another embodiment, a moiety useful in the invention is a drug delivery vehicle such as a chambered microdevice, liposome, cell or virus.

The matrix metalloproteinases responsible for degrading constituents of the extracellular matrix and digesting basement membranes are a family of related zinc-dependent enzymes. This protein family includes the collagenases, gelatinases, stromelysins, and membrane-type MMPs (MT-MMPs). The matrix metalloproteinases play roles in tissue remodeling and cell migration during morphogenesis and wound healing (Birkendal-Hansen, *Curr. Opin. Cell Biol.* 7:728-735 (1995)).

One step in the recruitment of endothelial cells during angiogenesis and in the formation of vascular tumors is the digestion of basement membranes by migrating endothelial cells. This process requires the presence of matrix-degrading enzymes, whose production by endothelial cells is often induced by angiogenic factors, and can assist in the penetration of capillary sprouts during tumor neoangiogenesis and facilitate the invasion of tumor cells through endothelia during metastasis.

Matrix metalloproteinases have been implicated in pathological processes in cells and tissues. For example, matrix metalloproteinases have been implicated in angiogenesis within tumors and tumor metastasis. In addition, this class of metalloproteinases has been implicated in a variety of other diseases listed below, including inflammatory diseases and diseases of the central nervous system. The invention provides selective polypeptide substrates for particular matrix metalloproteinases. These selective polypeptide substrates can be used to preferentially direct moieties to the sites of activity of these metalloproteinases. This preferential targeting can be used for diagnosis, prediction, prevention, monitoring, and treatment of diseases involving these metalloproteinases.

The gelatinases are a subset of matrix metalloproteinases that degrade denatured collagen (gelatin) and are associated with metastatic potential. Two gelatinases, which are also known as type IV collagenases, have been described: matrix metalloproteinase-2 (MMP-2; gelatinase A) and matrix metalloproteinase-9 (MMP-9; gelatinase B). Metastatic tumor cell lines express higher levels of gelatinases than nonmetastatic counterparts (Liotta et al., *Nature* 284:67-68 (1980); Karakiulakis et al., *Invasion & Metastasis* 17:158-168 (1997)). In addition, gelatinases are produced by nonmalignant cells present in a tumor, such as mesenchymal cells and tumor-infiltrating macrophages, as well as by endothelial cells (Pyke et al., *Am. J. Pathol.* 142:359-365 (1993); Sugiura et al., *Cancer Res.* 58:2209-2216 (1998); Wilhelm et al., *J. Biol. Chem.* 264:17213-17221 (1989); Heppner et al., *Am. J. Pathol.* 149:273-282 (1996); Brooks et al., *Cell* 85:683-693 (1996); Haas et al., *J. Biol. Chem.* 273:3604-3610(1998); Vu et al., *Cell* 93:411-422 (1998)). In animal models, inhibitors of matrix metalloproteinases prevent tumor dissemination as well as the formation of metastases (Davies et al., *Cancer Res.* 53:2087-2091 (1993); Taraboletti et al., *J. Natl. Cancer Inst.* 87:293-298 (1995); Volpert et al., *J. Clin. Invest.* 98:671-679 (1996); Anderson et al., *Cancer Res.* 56:715-710(1996); Ecclels et al., *Cancer Res.* 56:2815-2822 (1996)).

Evidence for the enhanced expression of MMP-2 in human tumors comes from experimental studies correlating enzyme expression and tumor grade (Liotta, et al., *Nature*, 284:67-68 (1980); Nakajima et al., *Cancer Research*, 47:4869-4876 (1987); Turpeenniemi-Hujanen, et al., *J. Natl Cancer Inst.*, 75:99-103 (1985)). For example, immunocytochemical and in situ hybridization studies have shown increased expression of MMP-2 in many human tumors, including carcinomas of the colon (Poulsom et al., *Amer. J. Pathol.*, 141:389-396 (1992); Pyke et al., *Amer. J. of Pathol.*, 142:359-365 (1993)), pancreas (Gress et al., *Intl J. Cancer*, 62:407-413 (1995)), prostate (Boag and Young, *Amer. J. Pathol.*, 144:585-591 (1994)), bladder (Davies et al., *Cancer Res.*, 53:5365-5369 (1993)), breast (Davies et al., *Brit. J. Cancer* 67:1126-31 (1993); Polette, et al., *Virchows Archiv.*, 424: 641-645 (1994)), skin (squamous and basal cell carcinomas) (Pyke, et al., *Cancer Res.*, 52:1336-1341(1992)), and ovary (Autio-Harmainen et al., *Lab. Invest.* 69,:312-321(1993)). MMP-9 has been found to be expressed in tumors from diverse sites, including skin, lungs, breast, colo-rectum, liver, prostate, brain, bone marrow, and bone (Pyke, et al., *Cancer Res.*, supra (1992); Ashida et al., *Amer. J. Pathol.*, 149:1803-1811 (1996); Canete-Soler et al. *Amer. J. Pathol.*, 144:518-527 (1994); Iwata et al., *Japanese J. Cancer Res.*, 87: 602-611 (1996); Nakagawa et al., *Japanese J. Cancer Res.* 85:934-938 (1994); Soini et al., *J. Histochem. & Cytochem.*, 42:945-951 (1994)).

In addition to its role in metastasis, MMP-2 also plays a role in angiogenesis. MMP-2 has been shown to be involved in a pathway involving the release of endoperoxide/thromboxane A2 and ADP (Siess, *Physiolog. Rev.*, 69: 58-178 (1989); Colman, *FASEB Journal* 4:1425-1435 (1990); Sargeant and Sage, *Pharm. & Therapeut.*, 64:395-443 (1994)). The release of MMP-2 was shown to mediate platelet aggregation in vitro implicating MMP-2 in possible anti-thrombotic therapies.

In addition to playing a role in cancer, matrix metalloproteinases can be involved in other pathologies, for example, in arthritis or in neurodegenerative diseases such as multiple sclerosis (Firestein, *Curr. Opin. Rheumatol.* 4:348-354 (1992); Gijbels et al., *J. Neuroimmunol.* 41:29-34 (1992)). For example, high levels of MMP-9 have been detected in serum and synovial fluid of patients with inflammatory arthritis such as rheumatoid arthritis compared to healthy patients or patients with osteoarthritis (Ahrens et al., *Arthritis & Rheumatism* 39:1576-87 (1996); Gruber et al., *Clin. Immunol. & Immunopathol.*, 78:161-171 (1996)). In addition, a correlation has been reported between the arthritic activity score of a joint and the amount of MMP-9 in the aspirated synovial fluid (Koolwijk et al. *J. Reumatology*, 22:385-393 (1995)).

Expression of MMP-9 is also detected in diseases of the nervous system. For example, prominent expression of MMP-9 has been found in reactive astrocytes and macrophages in demyelinating lesions compared to normal brain tissue (Cuzner et al., *J. Neuropathol. Exp. Neurol*, 55:1194-1204 (1996)). MMP-9 is elevated in encephelomyelitis (Gijbels, et al., *J. Neuro. Res.* 36:432-440 (1993); Proost, et al., *Biochem, Biophys, Res. Comm.* 192:1175-1181 (1993)), in the cerebrospinal fluid of patients with multiple sclerosis (Leppert, et al., *Brain* 121:2327-2334 (1998); Rosenberg et al., *Brain Res.*, 703:151-155(1995)), and in patients with AIDS-related dementia (Conant, et al., *Annals of Neurology* 46: 391-398 (1999)). Furthermore, in patients with amyotrophic lateral sclerosis, MMP-9 expression is found in the pyramidal neurons of the motor cortex and in the motor neurons of the spinal cord (Lim et al., *J. Neurochem.*, 67:251-259 (1996)).

MMP-9 has also been associated with a variety of other inflammatory diseases. For example, a high level of MMP-9 activity is found in the vessel wall of aortic aneurysms (Freestone, et al. *Arteriosclerosis, Thrombosis & Vascular Biology*, 15:1145-1151 (1995); Newman et al., *Connective Tissue Research*, 30:265-276,(1994); Sakalihasan et al., *J. Vascular Surgery*, 24:127-33 (1996)). In addition, patients with giant cell arteritis have increased levels of MMP-9, and MMP-9 mRNA is found in smooth muscle cells and fibroblasts in the regions of fragmented elastic tissue in the lamina media of inflamed vessels (Sorbi, et al., *Arthritis & Rheumatism*, 35:1747-1753 (1996)). Increased levels of MMP-9 are also found in sputum of patients with cystic fibrosis and in bronchoalveolar lavage fluids of those with bronchiectasis (Delacourt et al., *Amer. J. Respiratory & Critical Care Med.*, 152: 765-764 (1995); Sepper et al, *Chest*, 106:1129-1133 (1994)). High levels of MMP-9 have also been found in blister fluids from the skin lesions of bullous pemphigoid patients (Stahle-Backdahl et al., *J. Clinical Invest.*, 93:2022-2030 (1994)).

MMP-9 expression has also been implicated in the pathogenesis of several other diseases. For example, MMP-9 has been implicated in polycystic kidney disease (Murray et al., *Conn. Tissue Res.*, 33:249-256 (1996)), membranous nephropathy (McMillin et al., *J. Clin. Invest.*, 97:1094-1101 (1996)), and Alzheimer's disease (Lim et al., *J. Neurochem.*, 68:1606-1611 (1997)).

MMP-2 is a widely distributed matrix metalloproteinase and is produced constitutively by many cells in culture. MMP-9 can be secreted by mesenchymal cells in culture after induction by cytokines and other agents, is a major product of monocytes and tumor cells, and is present in the granule fraction of polymorphonuclear leukocytes. Both MMP-2 and MMP-9 can be detected in plasma, and MMP-9 has been shown to be present in saliva. Although MMP-2 and MMP-9 can have overlapping substrate specificities and localization patterns, they are differentially regulated (Murphy and Crabbe, supra, 1995).

Both MMP-2 and MMP-9 show a modular structure typical of the matrix metalloproteinase family. Both MMP-2 and MMP-9 contain a signal sequence; an amino-terminal propeptide responsible for the maintenance of latency in the proenzyme, which is removed by exogenous and endogenous proteolytic cleavages to produce the active enzyme form; a catalytic domain containing zinc and calcium binding sites, which is common to all matrix metalloproteinases (Collier et al., *Genomics* 9:429 (1991); Matrisan, *Bioessays* 14:455 (1992)), and some MMPs also contain a hemopexin domain near the carboxyl-terminus. In MMP-2, the carboxy-terminal domain functions in cell binding and in binding to a tissue inhibitor of metalloproteinases (TIMP). In MMP-9, the carboxy-terminal domain is important for TIMP and collagen binding activity. MMP-2 and MMP-9 are unique among the metalloproteinases in containing a gelatin-binding domain, which is inserted within the catalytic domain and has homology to the three type II repeats of the gelatin-binding region of fibronectin (Collier et al., supra, 1988; Wilhelm et al., supra, 1989; and Collier et al., *J. Biol. Chem.* 267:6776 (1992)). This domain confers the matrix and macromolecular substrate binding specificity on the gelatinases (Collier et al. supra, 1991). An additional 54 amino acid proline-rich extension to the short proline-rich hinge region between the catalytic and carboxy-terminal domains is present in MMP-9 (Stetler-Stevenson et al., *Annual Rev. Cell Biol.* 9:541-573 (1993)).

The two gelatinases MMP-2 and MMP-9 have similar substrate specificities. In addition to gelatinolytic activities, they can degrade native collagens of types IV and V and are potent elastin-degrading enzymes. MMP-2 can additionally degrade, for example, collagen types VII and XI, aggrecan, fibronectin, laminin A and B chains, and myelin basic protein. MMP-9 can degrade, for example, type I, III and XI collagens; aggrecan; the laminin A chain, and myelin basic protein.

The location of amino acids within MMP cleavage sites are described in relation to the peptide bond that is hydrolyzed (see FIG. 1). For example, the amino acid on the amino terminal side of the hydrolyzed bond is denoted as $P_1$ and the amino acid on the carboxyl terminal side of the hydrolyzed bond is denoted at $P_{1'}$. The amino acid just upstream of $P_1$ is denoted as $P_2$ and the amino acid just downstream of $P_{1'}$ is denoted as $P_{2'}$, and so on for additional amino acids. The amino acid residues that flank the scissile bond, which is the bond hydrolyzed by the proteinase, within a substrate are involved in the selectivity of that substrate for a given proteinase. Therefore, substrates can be described by both their primary amino acid sequence and by the position of amino acids within that sequence relative to the hydrolyzed bond. MMP-2 and MMP-9 appear to have a similar substrate recognition specificity: a small amino acid such as Gly or Ala is preferred at the $P_1$ site, while an alipahatic or hydrophobic residue is preferred at the $P_{1'}$ site (Murphy and Crabbe, supra, 1995).

Despite a high degree of structural homology, MMP-2 and MMP-9 are reported to have distinct biological roles. For example, in tumors in the RIP-Tag mouse, where both proteinases are present, only MMP-9 appears to be causally involved in the angiogenic switch of these tumors (Bergers et al., *Nature Cell Biol.* 2:737-744 (2000)). Similarly, in the process of platelet aggregation, MMP-2 promotes aggregation, but MMP-9 inhibits aggregation (Fernandez-Patron, et al., *Thrombosis and Haemostasis* 82:1730-1735 (1999)).

An understanding of the biological function of MMP-9 comes from the study of mice lacking this gene. For example, MMP-9 deficient mice have impaired ossification of the skeletal growth plate, a defect that has been partially attributed to poor vascularization of developing bone (Vu et al., *Cell* 93:411-422 (1998)). Studies on these mice also show that MMP-9 is essential for the recruitment of osteoclasts into developing bones (Ensig et al., *J. Cell Biol.*, 151:879-889 (2000)). Other work indicates that MMP-9 deficient mice are resistant to dermal blistering in a bullous pemphigoid model, an effect that has been attributed to the inability of these mice to cleave the SERPIN a1-proteinase inhibitor (Liu, et al., *Cell* 102:647-655 (2000)). Finally, recent studies in which the MMP-9 deficient mice were mated with transgenic mouse model of multistage carcinogenesis indicate that MMP-9 is part of the angiogenic "switch" that is involved in tumor growth (Bergers et al., *Nature Cell Biol.* 2:737-744 (2000); Coussens, et al., *Cell* 103:481-490 (2000))

In addition to the gelatinases, other matrix metalloproteinases play a role in cancer. Membrane type-1 matrix metalloproteinase (MT1-MMP) has been cloned as an activator of proMMP-2 (Sato, et al., *Nature* 370:61-65 (1994)) and reported to be expressed in various cancers (Okada et al. *Proc. Natl. Acad. Sci.* 92:2730-2734 (1995), and Nomura et al., *Cancer Res.* 55:3263-3266 (1995)), suggesting that the proMMP-2 activation by MT1-MMP can play a role in tumor cell invasion and metastasis. Additionally, MT1-MMP itself can digest many types of ECM proteins such as interstitial collagens, gleatin and proteoglycan (Ohuchi et al *J. Biol. Chem.* 272:2446-2451 (1997)). Therefore, MT1-MMP can play a dual role in the digestion of ECM through a direct cleavage of the substrate proteins and through activation of proMMP2.

An association between the expression of activated MT1-MMP and tumor metastasis has been found in numerous cancers. The role of MT1-MMP in this process has been demonstrated by both in vitro and in vivo observations. Transfection in vitro of MT-1 MMP into tumor cells enhances the invasiveness of these tumor cells compared with controls (Sato et al., *Nature* 370:61-5 (1994)). Also, elevated expression of MT1-MMP has been reported in various human carcinomas of the uterine cervix (Gilles et al., *Intl. J. Cancer* 65:209-13 (1996)), the stomach (Nomura et al., *Cancer Res.* 55:3263-6 (1995); Ohtani et al., *Intl. J. Cancer* 68:565-70 (1996)), the lung (Sato et al., supra 1994; Tokuraku et al., *Intl. J. Cancer* 64:355-9 (1995); Polette et al., *Virchows Archiv* 428:29-35 (1996); Nawrocki et al., *Intl. J. Cancer* 72:556-64 (1997)), the breast (Polette et al. supra 1996; Gilles et al., *Lab. Invest.* 76:651-60 (1997); Okada et al., *Proc. Natl. Aca. Sci.* (USA) 92:2730-4 (1995); Ueno et al., *Cancer Res.* 57:2055-60 (1997)), the colon (Okada et al., supra 1995), the head and the neck (Okada et al., supra 1995; Yoshizaki et al. *Cancer* 79:139-44 (1997)) and in malignant brain tumors (Yamamoto et al., *Cancer Res.* 56:384-92 (1996)). Further evidence of the role of MT1-MMP in tumorigenesis comes from experiments with transgenic mice that overexpress MT1-MMP in vivo. In these mice, the MT1-MMP gene was overexpressed in the mammary gland using the mouse mammary tumor virus long terminal repeat-promoter. The MT1-MMP transgenic mice displayed abnormalities in 82% of female mammary glands and these abnormalities were verified as lymphocytic infiltration, fibrosis, hyperplasia, alveolar structure disruption, dysplasia, and adenocarcinoma (Ha et al., Cancer Res. 61:984-90 (2001)).

Additionally, MT1-MMP-deficient (null) mice have defects in skeletal development and angiogenesis. In these mice, the craniofacial, axial, and appendicular skeletons were affected, leading to a short and domed skull, and marked deceleration of postnatal growth plates. Defective vascular invasion of cartilage can lead to enlargement of hypertrophic zones of growth plates and delayed formation of secondary ossification centers in the long bones. In addition, an absence of FGF-2-induced angiogenic response in the cornea was found in these null mice. This result indicates a role for MT-1 MMP in the initiation of angiogenesis. A similar defect of angiogenesis can cause the delayed development of secondary ossification centers and retarded resorption of growth plate cartilage in MT1-MMP null mice and indicates a role for MT1-MMP in blood vessel invasion into uncalcified cartilage (Zhou et al., *Proc. Natl. Aca. Sci.* (USA) 97:4052-7 (2000)).

In addition, MT1-MMP can have a role in inflammation. MT1-MMP expression is found elevated in reactive astrocytes following neurodegeneration in the mouse central nervous system (Rathke-Hartlieb et al., *FEBS Letters* 481:227-34 (2000)).

The present invention relates to the discovery of polypeptide substrates that are selective for MMP-2, MMP-9 or MT1-MMP. The invention further relates to linkage of these polypeptide substrates to moieties and methods for using these compositions to preferentially direct a moiety to a site of a particular MMP activity.

As used herein, the term "polypeptide" is intended to mean two or more amino acids covalently bonded together. A polypeptide of the invention therefore includes small polypeptides having a few or several amino acids as well as large polypeptides having several hundred or more amino acids. Usually, the covalent bond between the two or more amino acid residues is an amide bond. However, the amino acids can be joined together by various other means known to those skilled in the polypeptide and chemical arts. Therefore, the term polypeptide is intended to include molecules which contain, in whole or in part, non-amide linkages between amino acids, amino acid analogs, and peptidomimetics. Similarly, the term also includes cyclic polypeptides and other conformationally constrained structures. A polypeptide can also be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

A modification of a polypeptide can also include non-naturally occurring derivatives, analogues and functional peptidomimetics thereof generated by, for example, chemical synthesis. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by polypeptide bonds.

As used herein, the term "amino acid" is intended to mean both naturally occurring and non-naturally occurring amino acids as well as amino acid analogs and mimetics. Hydrophobic amino acids as referred to herein include, for example, leucine (L) isoleucine (I), valine (V), methionine (M), tyrosine (Y), phenylalanine (F), and tryptophan (W). Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids.

Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the ε-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997), the entire book of which is incorporated herein by reference. Yet other examples include amino acids whose amide portion and, therefore, the amide backbone of the resulting polypeptide, has been replaced, for example, by a sugar ring, steroid, benzodiazepine or carbo cycle. See, for instance, *Burger's Medicinal Chemistry and Drug Discovery*, Ed. Manfred E. Wolff, Ch. 15, pp. 619-620, John Wiley & Sons Inc., New York, N.Y. (1995), the entire book of which is incorporated herein by reference. Methods for synthesizing polypeptides and peptidomimetics are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference).

With respect to the polypeptides of the invention, peptidomimetics, which include chemically modified polypeptides, polypeptide-like molecules containing non-naturally occurring amino acids, peptoids and the like, have a functional activity substantially the same as the reference polypeptides upon which the peptidomimetic is derived (see, for example, "Burger's Medicinal Chemistry and Drug Discovery", 1995, supra). A peptidomimetic shows a considerable degree of structural identity when compared to the reference polypeptide and exhibits characteristics which are definitively recognizable or known as being derived from or related to the reference polypeptide.

The term "substantially the same" or "substantially" when referring to a functional activity means a considerable degree of the amount of functional activity, such as binding or extent of hydrolysis, is retained. For example, a peptidomimetic can retain a considerable degree of binding affinity to a metalloproteinase when compared to a reference selective substrate polypeptide. One of skill in the art will recognize if a level of activity of, for example, a peptidomimetic is substantially the same as that of a specific binding or selective substrate polypeptide depending on the assay used. Substantially the same when used in reference to a particular measurement is intended to mean that the referenced measurement is within a range of values encompassing the referenced value and within accepted standards of a credible assay within the art, or within accepted statistical variance of a credible assay within the art. For example, a peptidomimetic can have substantially the same activity as a reference polypeptide of the invention if it has one-one hundredth, one-fiftieth, one-tenth, one-half, the same, or two times, five times, ten times, fifty times or one hundred times the activity of the reference polypeptide. Peptidomimetics can provide various advantages over polypeptides, and are particularly useful for oral administration since they can be stable when administered to a subject during passage throughout the digestive tract.

The polypeptides of the invention can be provided in isolated form. As used herein in reference to a polypeptide of the invention, the term "isolated" means a polypeptide that is in a form that is relatively free from unrelated polypeptides as well as contaminating polypeptides, lipids, nucleic acids and other cellular material that normally are associated with the polypeptide in a cell or that are associated with the polypeptide in a library. An isolated polypeptide of the invention can be a pool containing a small number of related or unrelated polypeptides, provided that the pool contains at most fifteen polypeptides of different amino acid sequence, for example, five or ten polypeptides of different amino acid sequence.

As used herein, the term "specific binding polypeptide" is intended to mean a polypeptide that specifically binds to the active site of a matrix metalloproteinase with or without being hydrolyzed by the metalloproteinase. A specific binding polypeptide can interact with a metalloproteinase such that the specific binding polypeptide will have an affinity for the metalloproteinase that is measurably different from a non-specific interaction. A specific binding polypeptide that is hydrolyzed by a metalloproteinase is called a substrate. A specific binding polypeptide that is not hydrolyzed by a metalloproteinase, for example, a non-hydrolyzable variation of a substrate polypeptide, can also be used in the methods of the invention as described herein.

As used herein, the term "substrate" when used in reference to a metalloproteinase is intended to mean any material or substance on which a metalloproteinase acts. The material or substance can be, for example, a naturally or non-naturally occurring organic chemical such as a drug, or a macromolecule such as a polypeptide or peptidomimetic. A metalloproteinase substrate specifically interacts with one or more metalloproteinases, and is hydrolyzed by the metalloproteinase. At least one molecule of the substrate is hydrolyzed by the metalloproteinase using appropriate conditions within the time frame of an experiment. Additionally, 10%, 20%, 30%, 40%, 50%, 60%, 70%, 80%, 90%, or 100% of the substrate can be hydrolyzed by the metalloproteinase.

Hydrolysis of a substrate by a metalloproteinase is the conversion of a substrate into a product by an enzyme. The rate of hydrolysis can be measured using the same parameters used to measure enzyme kinetics (Fersht, *Enzyme Structure and Mechanism*, W. H. Freeman and Co. (1997)). For example, Michaelis-Menten parameters such as $k_{cat}$ and $K_m$ can be used to measure the rate of hydrolysis by proteinases. In the simple Michaelis-Menten mechanism in which there is only one enzyme-substrate complex and all binding steps are fast, $k_{cat}$ is a first-order rate constant for the chemical conversion of the enzyme-substrate complex to the enzyme-product complex. The constant $k_{cat}$ is referred to as the turnover number of the enzyme because it represents the maximum number of substrate molecules converted to products per active site per unit time, or the number of times the enzyme "turns over" per unit time. The $K_m$ is the substrate concentration at which the rate of the reaction is equal to one-half of the maximal rate (v=Vmax/2). The $K_m$ is an apparent dissociation constant that can be treated as the overall dissociation constant of all enzyme-bound species. Therefore, the $K_m$ is indicative of the binding affinity of the substrate for the enzyme. A specificity constant or selectivity factor can be determined by dividing $k_{cat}$ by $K_m$. Thus, $k_{cat}/K_m$ is an apparent second-order rate constant and is used herein to describe the efficiency of hydrolysis.

In order for hydrolysis to occur, the metalloproteinase and substrate interact specifically such that the substrate will have an affinity for the metalloproteinase that is measurably different from a non-specific interaction. Binding affinity of a substrate to a metalloproteinase can be indirectly assessed by measuring $K_m$. A substrate can interact with the active site of a metalloproteinase with either low or high affinity, for example, a $K_m$ of about $10^{-3}$ M to about $10^{-7}$ M indicates lower affinity while a $K_m$ of at least about $10^{-7}$ M, at least about $10^{-8}$ M, at least about $10^{-9}$ M, at least about $10^{-10}$ M, or at least about $10^{-11}$ M or $10^{-12}$ M or greater indicates higher affinity. The polypeptide substrates of the invention can have utility as targeting agents because of the product of two parameters, binding affinity and the rate of hydrolysis. Therefore, changes in binding affinity can compensate for changes in hydrolysis rate and changes in hydrolysis rate can compensate for changes in binding affinity. For example, even polypeptides with low affinity for the active site of a MMP can be useful in the invention for targeting a moiety, provided the rate of hydrolysis of the polypeptide is high.

As used herein, the term "selective substrate" when used in reference to a metalloproteinase substrate molecule is intended to mean that the substrate molecule is hydrolyzed at least three-fold more efficiently by one metalloproteinase than by another metalloproteinase. A selective substrate is a substrate for a particular metalloproteinase, but is not substantially a substrate for at least one other metalloproteinase. In addition, selective substrate molecules can be a substrate for a particular metalloproteinase, but not a substrate for at least two or more other metalloproteinases. Additionally, a selective substrate can be hydrolyzed more than three-fold more efficiently by one metalloproteinase than by another.

The hydrolysis of a selective substrate by a group of closely related matrix metalloproteinases, such as the gelatinases, or by a distantly related group of matrix metalloproteinases can be determined. A selective substrate that is hydrolyzed by a particular metalloproteinase, but not substantially hydrolyzed by a group of closely related metalloproteinases can be considered a more selective substrate than a selective substrate that is hydrolyzed by a particular metalloproteinase, but not by a group of distantly related metalloproteinases. In addition, a substrate that is hydrolyzed by a particular metalloproteinase, but not substantially hydrolyzed by several other metalloproteinases can be considered a more selective substrate than a metalloproteinase that is hydrolyzed by a particular metalloproteinase but not substantially hydrolyzed by one other metalloproteinase.

A selective substrate can be a substrate for a particular metalloproteinase, but not substantially a substrate for more than one other metalloproteinase. For example, a selective substrate can be a substrate for a particular metalloproteinase, but not a substrate for at least two other metalloproteinases, at least three other metalloproteinases, at least four other metalloproteinases, at least five other metalloproteinases, at least ten other metalloproteinases, or any other metalloproteinases tested. Additionally, a selective substrate can be hydrolyzed more than three-fold more efficiently by one metalloproteinase than by another. For example, a selective substrate can be hydrolyzed four-fold, five-fold, ten-fold, fifty-fold, one hundred-fold, two hundred-fold or more efficiently by one metalloproteinase than by another metalloproteinase. A selective substrate that is hydrolyzed more than three-fold more efficiently by one metalloproteinase compared to another can be considered a more selective substrate than a substrate that is hydrolyzed three-fold more efficiently by one metalloproteinase compared to another. The hydrolysis efficiency of a selective substrate by a group of closely related matrix metalloproteinases, such as the collagenases, or a distantly related group of matrix metalloproteinases can be determined.

Known matrix metalloproteinases families include, for example, the collagenases, gelatinases, stromelysins, and membrane-type metalloproteinases (Parks, *Matrix Metalloproteinases. Biology of Extracellular Matrix Series*, Ed. Mecham, R. P., Academic Press, Inc., San Diego, Calif. (1998)). The collagenases include collagenase 1 (MMP-1), collagenase 2 (MMP-8), collagenase 3 (MMP-13) and collagenase 4 (MMP-18). As stated earlier the gelatinases include gelatinase A (MMP-2) and gelatinase B (MMP-9). The stromelysins include stromelysin 1 (MMP-3), stromelysin 2 (MP-10), and stromelysin 3 (MMP-11). The membrane-type metalloproteinases include MT-1-MMP, also called MT1-MMP, (MMP-14), MT-2 MMP (MMP-15), MT-3 MMP (MMP-16), and MT-4 MMP (MMP-17). Other matrix metalloproteinases include, for example, matrilysin (MMP-7), metalloelastase (MMP-12), enamelysin (MMP-20) and MMP-19.

The efficiency of substrate hydrolysis is measured by determining the $k_{cat}/K_m$ ratio for each metalloproteinase. Different assay protocols can be used to determine hydrolysis rate with significantly different results, so the same assay protocol is used for all metalloproteinases that are to be directly compared. For example, the hydrolysis rate assays exemplified herein utilize an unlabelled substrate for cleavage and then after cleavage the product is labeled and detected. Variations of this assay include using a labeled substrate, such as a fluorogenic substrate, for the cleavage reaction (Deng et al., *J. Biol. Chem.*, 275:31422-31427 (2000)). However, this type of protocol can result in different hydrolysis rates even when using the same substrate sequence and the same metalloproteinase enzymes as the protocol exemplified herein.

A variety of methods known in the art can be used to determine the percent hydrolysis of a substrate by a metalloproteinase, the efficiency of hydrolysis of a substrate by a metalloproteinase, and the affinity of a metalloproteinase to a specific binding polypeptide or substrate. For example, methods and conditions suitable for determining the hydrolysis of a substrate by MT1-MMP, MMP-2, and MMP-9 are described in Examples II, III, and IV herein.

One skilled in the art will understand that variations of substrate polypeptides can be made by methods well known in the art and as described herein, where the resulting polypeptide or peptidomimetic is no longer hydrolyzed by the metalloproteinase. When the specific binding polypeptide is not hydrolyzed by the metalloproteinase, its binding affinity can be measured by the dissociation constant $k_d$. A specific binding polypeptide can interact with the active site of a metalloproteinase with either low or high affinity, for example, a $k_d$ of about $10^{-3}$ M to about $10^{-7}$ M indicates lower affinity while a $k_d$ of at least about $10^{-7}$ M, at least about $10^{-8}$ M, at least about $10^{-9}$ M, at least about $10^{-10}$ M, or at least about $10^{-11}$ M or $10^{-12}$ M or greater indicates higher affinity. Specific binding can be measured, for example, by determining the binding of a metalloproteinase to a specific binding polypeptide compared to binding to a control polypeptide. The control polypeptide is generally a molecule of similar structure to the specific binding polypeptide that does not have binding activity, for example, a polypeptide of similar size that lacks the correct consensus motif. Specific binding can involve non-covalent or covalent interactions between the metalloproteinase and the specific binding polypeptide.

While the invention is described below with specific embodiments to selective substrate polypeptides, it is understood that specific binding polypeptides which are not hydrolyzed can also be used similarly in the methods of the invention as described herein.

The invention provides selective substrate polypeptides for MT1-MMP, MMP-2 and MMP-9. Polypeptide substrates for metalloproteinases can be selected using several screening, and screening with affinity capture, methods. For example, polypeptide substrates for metalloproteinases can be selected using a phage displayed polypeptide library with a tag such as a 6×his affinity tag or a FLAG epitope tag as a tether (Kridel et al., *Anal. Biochem.* 294:176-184 (2001); Kridel et al., *J. Biol. Chem.* 276:20572-10578 (2001)).

Polypeptide substrates for MT1-MMP, MMP-2 or MMP-9 were selected herein from a collection of degenerate polypeptides displayed on filamentous phage (see Examples I, II, III, and IV). In general, substrate phage libraries were generated using a modified version of the fUSE5 phagemid. Features of the library were a random polypeptide hexamer on the N-terminus of the gene III protein and a FLAG epitope positioned to the N-terminus of the hexamer. These and other features are described further in Example I. A substrate phage library was then incubated with an activated MMP (MT1-MMP, MMP-2, or MMP-9) and phage where the FLAG epitope had been cleaved were separated from phage still containing the FLAG epitope by incubating the phage samples with an anti-FLAG monoclonal antibody. The phage-antibody complexes were then precipitated. The phage where the FLAG eptiope had been cleaved remained in the supernatant and were amplified using *E. coli* and used for an additional round of substrate selection. Detailed descriptions of the methods used can be found in Examples II and III.

Polypeptide substrates for MMP-2, MMP-9 and MT1-MMP were identified using substrate phage display. The substrates are listed in Table I. In the construction of the phage hexamer library, the hexamer polypeptide was flanked at the amino terminus by serine (S) and glycine (G) and at the carboxyl-terminus by threonine (T) and alanine (A). These residues are listed in Table I only if they are within the $P_3$ to $P_{3'}$ positions of the substrate polypeptide. With the exception of SEQ ID NO:30, the threonine or threonine and alanine at the carboxyl-terminus of these polypeptide sequences are the result of the library construction and one skilled in the art will understand that other residues could be substituted at these positions. The percent hydrolysis by the indicated metalloproteinase as determined using a substrate phage ELISA is shown. The substrate phage ELISA measures the extent of hydrolysis of a hexamer polypeptide substrate by the candidate metalloproteinase over a determined time period. Briefly, a 96 well microtiter plate is coated with anti-M13 antibody and supernatant from a phage culture is added to each well and incubated to allow the FLAG-hexamer phage to bind to the well. Unbound phage are washed away and proteolysis incubation buffer is added with or without the metalloproteinase of interest. To measure hydrolysis of the polypeptides by the proteinase, an anti-FLAG antibody is added to each well and binding of the antibody to an exposed FLAG epitope is measured using a HRP-conjugated goat anti-rabbit antibody followed by detection in a spectrophotometer at 490 nm. The extent of hydrolysis is calculated by the ratio of the optical density (O.D.) at 490 nm of the proteinase-treated wells compared to the wells lacking proteinase. In addition, the position of the scissile bond as determined by mass spectrometry analysis of the cleavage products from synthesized representative polypeptides is indicated in Table I using the nomenclature of Schecter and Berger. Determination of the position of the scissile bond by mass spectrometry analysis is described further in Example V.

Other methods also can be used to measure the percent hydrolysis of a substrate by a metalloproteinase including, for example, using a synthesized selective substrate polypeptide instead of a phage particle presenting a selective substrate polypeptide. In addition, several methods known in the art can be used to measure specific hydrolysis by a metalloproteinase. A variety of different assay formats are available for these methods.

The polypeptides listed in Table I are MMP specific binding polypeptides since they specifically interact with the indicated MMP. In addition, the polypeptides listed in Table I are MMP substrates since they are hydrolyzed by the indicated MMP. Furthermore, the polypeptides listed in Table I can be selective MMP substrates since representative polypeptides from Table I have been shown in Table II to be hydrolyzed at least three-fold more efficiently by a particular MMP compared to another MMP.

TABLE I

| SEQ ID NO: | Phage clone | MMP-2 Polypeptide Substrates | | | P3 | P2 | P1 | P1' | P2' | P3' | | % hydrolysis |
|---|---|---|---|---|---|---|---|---|---|---|---|---|
| 1 | B49 | | | | L | R | L | A | A | I | T | A | | 100 |
| 2 | B74 | | | | E | S | L | A | Y | Y | T | A | | 81 |
| 3 | A54 | | | | P | M | I | S | V | L | T | A | | 98 |
| 4 | B54 | | | | | S | L | H | S | I | I | T | | 72 |
| 5 | B79 | | | | S | D | I | R | M | L | T | A | | 64 |
| 6 | B66 | | | | F | N | L | Y | N | L | T | A | | 51 |
| 7 | B46 | | | | | Y | L | Q | V | L | L | T | | 48 |
| 8 | A43 | | | | | | I | V | N | L | Y | P | | 38 |
| 9 | A6 | | | | V | G | L | I | A | I | T | A | | 30 |
| 41 | | | | | | | I/L | X | X | X_{Hx} | | | | |

| 10 | C9 | | | | R | S | L | S | R | L | T | A | | 100 |
| 11 | A34 | | | | N | R | Y | S | S | L | T | A | | 100 |
| 12 | A13 | | | | G | A | V | S | W | L | L | T | | 100 |
| 13 | B37 | | | | A | N | I | S | D | L | T | A | | 97 |
| 14 | A31 | | | | W | T | S | S | W | L | T | A | | 100 |
| 15 | B53 | | | | T | I | L | S | L | L | T | A | | 73 |
| 16 | C3 | | | | | F | N | S | M | L | K | T | | 28 |
| 42 | | | | | | | X | S | X | L | | | | |
| 17 | A21 | | | | H | M | H | K | A | L | T | A | | 30 |
| 18 | C5 | | | | | L | H | R | R | I | D | T | | 60 |
| 19 | A9 | | | | | M | H | S | R | P | P | T | | 50 |
| 20 | A21 | | | | H | M | H | K | A | L | T | A | | 30 |
| 21 | A4 | | | | | R | H | L | G | L | Q | T | | 30 |
| 22 | C6 | | | | | L | H | K | K | V | H | T | | 19 |
| 23 | D3 | | | | | A | H | A | K | H | W | T | | 13 |
| 43 | | | | | | | H | X | X | X_{Hx} | | | | |
| 24 | A3 | | | | A | K | P | R | A | L | T | A | | 100 |
| 25 | A45 | | | | | | P | Y | V | I | W | L | | 100 |
| 26 | A10 | | | | E | Y | E | H | M | R | T | A | | 80 |
| 27 | A29 | | | | I | Y | L | G | W | A | T | A | | 100 |

TABLE I-continued

| | | MMP-9 Polypeptide Substrates | | | | | | | | | | | |
|---|---|---|---|---|---|---|---|---|---|---|---|---|---|
| 28 | C15 | | | K | G | P | R | Q | I | T | A | | 100 |
| 29 | A11 | | | K | I | P | R | T | L | T | A | | 100 |
| 30 | A6 | | | | | P | R | A | V | S | T | | 100 |
| 31 | D12 | | | | | P | R | P | L | S | G | | 100 |
| 32 | D36 | | | F | R | P | R | S | I | T | A | | 91 |
| 33 | D24 | | | | | P | R | S | I | S | N | | 85 |
| 34 | D5 | | | N | P | P | R | Y | L | T | A | | 60 |
| 35 | D17 | | | S | V | P | R | H | F | T | A | | 67 |
| 44 | | | | | | P | R | R | $X_{Hx}$ | S/T | | | |
| | | MT1-MMP Polypeptide Substrates | | | | | | | | | | | |
| 36 | A42 | | | | | R | I | G | F | L | R | T | 88 |
| 37 | B175 | | | | | R | A | M | H | M | Y | T | 79 |
| 38 | A176 | | | | | R | S | E | N | I | R | T | 79 |
| 39 | B149 | | | | A | R | Y | R | W | L | T | A | 72 |
| 40 | B96 | | | | | L | I | S | H | S | I | T | A | 73 |

The invention provides isolated substrate polypeptides for MMP-2, MMP-9 or MT1-MMP containing an amino acid sequence selected from the group consisting of SEQ ID NOS: 1-47. For example, polypeptide substrates for MMP-2 were identified using substrate phage display as described in Example II. MMP-2 substrate polypeptides are exemplified by SEQ ID NOS:1-27. As shown in Table I, four distinct sets of substrates were identified. The first set contains the (I/L)-X-X-$X_{Hy}$ (SEQ ID NO: 41) consensus motif where X is any amino acid and $X_{Hy}$ is any hydrophobic amino acid and where $X_{Hy}$ is the $P_{1'}$ substituent of the substrate. Hydrophobic amino acids include, for example, leucine (L), isoleucine (I), valine (V), methionine (M), tyrosine (Y), phenylalanine (F), and tryptophan (W). Substrates in the second group contain a consensus motif with a sequence of X-S-X-L (SEQ ID NO: 42) where L is the $P_{1'}$ substituent of the substrate, and the third set of substrates contain the H-X-X-$X_{Hy}$ consensus sequence (SEQ ID NO: 43) where $X_{Hy}$ is the $P_{1'}$ substituent of the substrate.

Extended consensus sequences can also be derived from the polypeptide sequences in Table I. In addition, the invention provides an isolated MMP-2 substrate polypeptide comprising an amino acid sequence (I/L)-X-X-$X_{Hy}$-(T/L/I/Y)-X (SEQ ID NO:45), where $X_{Hy}$ is the $P_{1'}$ substituent of the substrate, X-S-X-$X_{Hy}$-(T/L/K)-X (SEQ ID NO:46), where $X_{Hy}$ is the $P_{1'}$ substituent of the substrate, and H-X-X-$X_{Hy}$-X-(T/A) (SEQ ID NO:47) where $X_{Hy}$ is the $P_{1'}$ substituent of the substrate.

A similar unbiased phage display approach as described in Example III was used to define the substrate recognition preference of MMP-9. These polypeptides are listed in Table I and designated as SEQ ID NOS:28-35. MMP-9 substrates containing the consensus motif P-R-X-$X_{Hy}$-(S/T) (SEQ ID NO: 44) that occupy positions $P_3$ through $P_{2'}$ are shown in Table I where $X_{Hy}$ is the $P_{1'}$ substituent of the substrate. A general consensus motif of P-X-X-$X_{Hy}$ has been shown to be cleaved non-selectively by a number of different MMPs and is presumed to represent a collagen-like substrate (Netzel-Arnett et al., *J. Biol. Chem.* 266:6747-6755 (1991); Netzel-Arnett et al., *Biochemistry* 32:6427-6432 (1993); Smith et al., *J. Biol. Chem.* 270:6440-6449 (1995)). The consensus motif shown in Table I is unique in that an arginine (R) is found at the $P_2$ position. When arginine is present at the $P_2$ position, the polypeptides become selective substrates for MMP-9. In addition, representative synthesized polypeptides containing the sequences of SEQ ID NOS:28, 29, and 30 have been shown in Table II to be selective substrate polypeptides for MMP-9. Polypeptide substrates for Membrane type-Matrix Metalloproteinase 1 (MT1-MMP) were identified using a similar substrate phage display assay as described in Example IV. These polypeptides are listed in Table I and designated as SEQ ID NOS:36-40.

In order to measure the selectivity of individual substrates for one metalloproteinase over another, representative polypeptides from the selected phage were synthesized and their rate of hydrolysis by several matrix metalloproteinases was determined. In some cases these representative polypeptide sequences contained an amino-terminal serine (S) and glycine (G) and/or a carboxyl-terminal threonine (T) and alanine (A) since these residues were used in the construction of the phage substrate library, although one skilled in the art will understand that other amino acid residues could be substituted at these positions. The kinetic parameters of substrate hydrolysis were measured using a fluorescamine incorporation assay that has been described previously (Ding et al., *PNAS*, 92:7627-7631 (1995); Coombs et al., *Chem. and Biol.* 5:475-488 (1998); Fields et al., *J. Biol. Chem.*, 262:6221-6226 (1987); Netzel-Arnett., et al. *J. Biol. Chem.*, 266:6747-6755 (1991)). Briefly, individual metalloproteinases were incubated with the individual polypeptide substrates at concentrations ranging from 100-800 μM. At selected time points the reactions were stopped by the addition of 1,10 phenanthroline. Polypeptide hydrolysis was determined by the addition of fluorescamine followed by detection at an excitation wavelength of 355 nm and an emission wavelength of 460 nm. The data were transformed to double reciprocal plots (1/[S] vs 1/$v_i$) to determine $K_m$ and $k_{cat}$. In some cases $K_m$ and $k_{cat}$ could not be determined individually, but the specificity constant, $k_{cat}/K_m$, was derived by the equation: $k_{cat}/K_m = v_i/[E_0][S_0]$ (Netzel-Arnett, supra, and Zumla et al., *J. Immunol. Methods* 149:69-76 (1992)).

The selectivity ratio of each polypeptide substrate was calculated by dividing the $k_{cat}/K_m$ value for one matrix metalloproteinase by the $k_{cat}/K_m$ value for the other matrix metalloproteinases that were tested. As shown in Table II, all of the representative polypeptides exhibit selectivity for one matrix metalloproteinase compared to at least one other matrix metalloproteinase. In many cases the polypeptide substrates are selective for one matrix metalloproteinase compared to several other matrix metalloproteinases.

TABLE II

| ID | Clone | P3 | P2 | P1 | P1' | P2' | P3' | MMP-9 | MMP-7 | MMP-13 |
|---|---|---|---|---|---|---|---|---|---|---|
| | | | | MMP-2 substrates | | | | | | |
| 24 | A3 | A | K | P | R | A | L | T | A | 2 | 21 | 14 |
| 1 | B49 | L | R | L | A | A | I | T | A | 14 | 6 | 13 |
| 2 | B74 | E | S | L | A | Y | Y | T | A | 108 | 354 | 140 |
| 10 | C9 | R | S | L | S | R | L | T | A | 198 | 35 | 52 |
| 11 | A34 | N | R | Y | S | S | L | T | A | 40 | 84 | 24 |
| 12 | A13 | G | A | V | S | W | L | L | T | 15 | 13 | 28 |
| 13 | B37 | A | N | I | S | D | L | T | A | 71 | 17 | 58 |
| 17 | A21 | H | M | H | K | A | L | T | A | 8 | | |
| | | | | MMP-9 Substrates | | | | | | |
| 28 | C15 | | K | P | R | Q | I | T | A | | 14 | 12 |
| 29 | A11 | K | I | P | R | T | L | T | A | | 10 | 3 |
| 30 | A6 | | | P | R | A | V | S | T | | 47 | 5 |
| | | | | MT1-MMP Substrates | | | | | | |
| 36 | A42 | | R | I | G | F | L | R | T | 54 | | |
| 37 | B175 | | R | A | M | H | M | Y | T | 19 | | |
| 38 | A176 | | R | S | E | N | I | R | T | 73 | | |
| 39 | B149 | A | R | Y | R | W | L | T | A | 3 | | |
| 40 | B96 | L | I | S | H | S | I | T | A | 5 | | |

The invention provides isolated MMP-2, MMP-9, or MT1-MMP selective substrate polypeptides containing an amino acid sequence selected from the group consisting of SEQ ID NOS: 1-47. For example, the invention provides an isolated MMP-2 selective substrate polypeptide containing an amino acid sequence selected from the group consisting of: SEQ ID NOS:1, 2, 10, 11, 12, 13, 17, and 24, or a functional peptidomimetic thereof. The invention also provides an isolated MMP-2 selective substrate polypeptide from Table II, where the polypeptide is a substrate for MMP-2, but is not a substrate for MMP-7, MMP-9, or MMP-13. In total, these data demonstrate the selectivity of polypeptides SEQ ID NOS:1, 2, 10, 11, 12, 13, 17, and 24 for MMP-2.

The invention further provides an isolated MMP-2 selective substrate polypeptide containing an amino acid sequence selected from the group consisting of: SEQ ID NOS:1-27, or a functional peptidomimetic thereof. The invention also provides an isolated MMP-2 selective substrate polypeptide comprising an amino acid sequence (I/L)-X-X-$X_{Hy}$ (SEQ ID NO:41), where $X_{Hy}$ is the $P_{1'}$ substituent of the substrate, X-S-X-L (SEQ ID NO:42), where leucine (L) is the $P_{1'}$ substituent of the substrate, and H-X-X-$X_{Hy}$ (SEQ ID NO:43) where $X_{Hy}$ is the $P_{1'}$ substituent of the substrate. In addition, the invention provides an isolated MMP-2 selective substrate polypeptide comprising an amino acid sequence (I/L)-X-X-$X_{Hy}$-(T/L/I/Y)-X (SEQ ID NO:45), where $X_{Hy}$ is the $P_{1'}$ substituent of the substrate, X-S-X-$X_{Hy}$-(T/L/K)-X (SEQ ID NO:46), where $X_{Hy}$ is the $P_{1'}$ substituent of the substrate, and H-X-X-$X_{Hy}$-X-(T/A) (SEQ ID NO:47) where $X_{hy}$ is the $P_{1'}$ substituent of the substrate.

Representative MMP-9 selective substrate polypeptides are listed in Table II and designated as SEQ ID NOS:28, 29, and 30. The invention provides an isolated MMP-9 selective substrate polypeptide containing an amino acid sequence selected from the group consisting of: SEQ ID NOS:28, 29, and 30. In addition, the invention provides an isolated MMP-9 selective substrate polypeptide containing an amino acid sequence selected from the group consisting of: SEQ ID NOS:28, 29, and 30, or a functional peptidomimetic thereof. The invention also provides an isolated MMP-9 selective substrate polypeptide from Table II, where the polypeptide is a substrate for MMP-9, but is not a substrate for MMP-7 and MMP-13. In total, these data demonstrate the selectivity of polypeptides SEQ ID NOS:28, 29, and 30 for MMP-9.

The invention further provides an isolated MMP-9 selective substrate polypeptide containing an amino acid sequence selected from the group consisting of: SEQ ID NOS:28-35, or a functional peptidomimetic thereof. The invention also provides an isolated MMP-9 selective substrate polypeptide comprising an amino acid sequence P-R-X-$X_{Hy}$-(S/T) (SEQ ID NO:44), where $X_{Hy}$ is the $P_{1'}$ substituent of the substrate.

MT1-MMP selective substrate polypeptides are listed in Table II and designated as SEQ ID NOS:36, 37, 38, 39, and 40. The invention provides an isolated MT1-MMP selective substrate polypeptide containing an amino acid sequence selected from the group consisting of: SEQ ID NOS:36, 37, 38, 39, and 40, or a functional peptidomimetic thereof. The invention also provides an isolated MT1-MMP selective substrate polypeptide from Table II, where the polypeptide is a substrate for MT1-MMP, but is not a substrate for MMP-9. In total, these data demonstrate the selectivity of polypeptides SEQ ID NOS:36, 37, 38, 39, and 40 for MT1-MMP.

Several polypeptides can contain the sequences identified above as selective substrate polypeptides (SEQ ID NOS: 1-47) including full length polypeptides and polypeptides that are smaller than full length polypeptides. These polypeptides can be specific binding polypeptides and selective substrate polypeptides of the invention. Polypeptides that are smaller than full length polypeptides include polypeptides that lack only a single amino acid compared to the full length polypeptide. This deleted amino acid can be at either the amino- or carboxyl-terminus of the full length polypeptide or at an internal residue in the polypeptide. In addition, the full length polypeptides can be active, such as polypeptides that have enzymatic activity, or the polypeptides can be inactive, for example, a denatured polypeptide. The invention further provides an isolated MMP-2, MMP-9, or MT1-MMP selective substrate polypeptide containing an amino acid sequence selected from the group consisting of: SEQ ID NOS: 1-47 where the polypeptide has a number of amino acids that is less than about 100 amino acids, less than about 40 amino acids, less than about 20 amino acids, or less than about 10 amino acids, or a functional peptidomimetic thereof.

The invention provides isolate MMP selective substrate polypeptides linked to a moiety. In addition, to selective substrate polypeptides, the invention also provides MMP specific binding polypeptides linked to a moiety. Further, the invention provides an isolated MMP-2, MMP-9, or MT1-MMP selective substrate polypeptide consisting of SEQ ID NOS: 1-47, or a functional peptidomimetic thereof, linked to a moiety.

The invention provides an isolated MMP-2 selective substrate polypeptide consisting of an amino acid sequence selected from the group consisting of: SEQ ID NOS:1, 2, 3, 10, 11, 12, 13, 17, and 24, or a functional peptidomimetic thereof, linked to a moiety. In addition, the invention provides an isolated MMP-2 selective substrate polypeptide consisting of an amino acid sequence selected from the group consisting of: SEQ ID NOS: 1-27, or a functional peptidomimetic thereof, linked to a moiety. The invention also provides an isolated MMP-2 selective substrate polypeptide comprising an amino acid sequence selected from the group consisting of SEQ ID NOS: 41, 42, 43, 45, 46, and 47, linked to a moiety.

The invention also provides an isolated MMP-9 selective substrate polypeptide consisting of an amino acid sequence selected from the group consisting of: SEQ ID NOS: 28, 29, and 30, or a functional peptidomimetic thereof, linked to a moiety. In addition, the invention provides an isolated MMP-9 selective substrate polypeptide consisting of an amino acid sequence selected from the group consisting of: SEQ ID NOS: 28-35, or a functional peptidomimetic thereof, linked to a moiety. The invention also provides an isolated MMP-9 selective substrate polypeptide comprising SEQ ID NO:44 linked to a moiety. The invention further provides an isolated MT1-MMP selective substrate polypeptide consisting of an amino acid sequence selected from the group consisting of: SEQ ID NOS:36, 37, 38, 39, and 40, or a functional peptidomimetic thereof, linked to a moiety.

As used herein, the term "moiety" is intended to mean a physical, chemical, or biological material that is linked to an isolated polypeptide comprising a selective substrate for MT1-MMP, MMP-2 or MMP-9. One use for such a polypeptide linked to a moiety is to target a site of MT1-MMP, MMP-2 or MMP-9 activity. Such a site of activity can be, for example, angiogenic vasculature, which can be tumor vasculature or other non-tumor vasculature. In particular, a moiety can be a biologically useful moiety such as therapeutic moiety or a drug delivery vehicle. Thus, a moiety can be a therapeutic moiety such as a cytotoxic agent or chemotherapeutic agent such as doxorubicin, which, when linked to an isolated polypeptide comprising a selective substrate for MT1-MMP, MMP-2 or MMP-9, provides a conjugate useful for treating a cancer in a subject. In addition, a moiety can be an diagnostic agent such as a radioactive or fluorescent agent. Furthermore, a moiety useful the invention can be a drug delivery vehicle such as a chambered microdevice, cell, liposome or virus, which can contain an agent such as a drug or a nucleic acid.

In addition, a moiety can be a material that is inactive as a therapeutic or diagnostic agent until it reaches a desired target location where it becomes activated. For example, a chemotherapeutic drug such as doxorubicin can be linked to a selective substrate polypeptide of the invention such that the drug is inactive. The selective substrate polypeptide can then target the inactive drug to a site, for example, a tumor, where the metalloproteinase for that substrate polypeptide can hydrolyze the substrate leading to activation of the drug. A diagnostic moiety can also be linked to a selective substrate polypeptide of the invention in an inactive form. This type of diagnostic moiety would be targeted to a site of metalloproteinase activity where it would be activated. For example, a fluorescent probe such as a near-infrared fluorescence (NIRF) imaging probe can be in an inactive or quenched state until it reaches a desired site where it can be converted to an active or un-quenched state.

A moiety also can be a molecule such as a polypeptide or nucleic acid, to which a MT1-MMP, MMP-2, or MMP-9 selective substrate is linked for the purpose of preferentially directing the polypeptide or nucleic acid to a site of MT1-MMP, MMP-2, or MMP-9 activity such as the angiogenic vasculature (Smith et al., *J. Biol. Chem.* 269:32788-32795 (1994); Goldman et al., *Cancer Res.* 15:1447-1451 (1997)). For example, a MMP-2 selective substrate polypeptide (such as SEQ ID NO: 1) can be expressed as a fusion protein with a desired polypeptide such that the MMP-2 selective substrate polypeptide (SEQ ID NO: 1) targets the grafted polypeptide to a site of MMP-2 activity. Such a desired polypeptide, which is grafted to the MMP-2 selective substrate polypeptide, can be a polypeptide involved in initiating cell death, for example, a toxin such as ricin, anthrax lethal factor, diphtheria toxin or pseudomaonas exotoxin, which, when linked to an MMP-2 selective substrate polypeptide, can selectively destroy a tissue expressing MMP-2. A MT1-MMP, MMP-2, or MMP-9 selective substrate polypeptide also can be grafted to a polypeptide expressed by a virus, for example, the adenovirus penton base coat protein, thus providing a means to target a virus to a site of an MMP activity such as a tumor (Wickham et al., *Gene Ther.* 2:750-756 (1995); Weitzman et al., "Gene Therapy and Vector Systems" 2:17-25 (1997)).

A moiety can be linked to a selective substrate polypeptide or specific binding polypeptide at any location within the polypeptide. For example, the moiety can be linked to the carboxyl terminus of the polypeptide, the amino terminus of the polypeptide, or at an internal site in the polypeptide. In addition, more than one moiety can be linked to the same polypeptide, for example, a moiety can be linked to the carboxyl terminus and another moiety, of the same or different type, can be linked to the amino terminus of the polypeptide. For example, a quenched fluorophore can be linked to the carboxyl terminus of a selective substrate polypeptide and an RGD polypeptide can be linked to the amino terminus in order to target the fluorophore to a site that binds RGD.

Chemistries used for the linkage of various moieties to polypeptides are well known in the art. A moiety such as a therapeutic moiety or diagnostic moiety can be linked to a MT1-MMP, MMP-2, or MMP-9 selective substrate polypeptide using, for example, carbodiimide conjugation (Bauminger and Wilchek, *Meth. Enzymol.* 70:151-159 (1980)). Carbodiimides comprise a group of compounds that have the general formula R—N=C=N—R', where R and R' can be aliphatic or aromatic, and are used for synthesis of polypeptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies. The water soluble carbodiimide, 1-ethyl-3-(3-dimethylaminopropyl) carbodiimide (EDC) is useful for conjugating a moiety to a MT1-MMP, MMP-2, or MMP-9 selective selective substrate polypeptide useful in the invention.

In addition to using carbodiimides for the direct formation of polypeptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger and Wilchek, supra, 1980).

Other methods for conjugating a moiety to a MT1-MMP, MMP-2, or MMP-9 selective substrate polypeptide useful in the invention also can be used. For example, sodium periodate oxidation followed by reductive alkylation of appropriate reactants can be used, as can glutaraldehyde crosslinking. However, it is recognized that, regardless of which method of producing a selective substrate polypeptide-moiety conjugate of the invention is selected, a determination must be made that the MT1-MMP, MMP-2, or MMP-9 selective substrate polypeptide maintains its selectivity and that the moiety maintains its relevant function.

The yield of MT1-MMP, MMP-2, or MMP-9 selective substrate polypeptide-moiety conjugate formed is determined using routine methods. For example, HPLC or capillary electrophoresis or other qualitative or quantitative method can be used (see, for example, Liu et al., *J. Chromatogr.* 735:357-366 (1996); Rose et al., *J. Chromatogr.* 425: 419-412 (1988)). In particular, the skilled artisan will recognize that the choice of a method for determining yield of a conjugation reaction depends, in part, on the physical and chemical characteristics of the specific moiety and MT1-MMP, MMP-2, or MMP-9 selective substrate polypeptide. Following conjugation, the reaction products are desalted to remove any free polypeptide and free drug.

In one embodiment, a moiety useful in the invention is a diagnostic moiety. The invention provides an isolated MMP-2 selective substrate polypeptide consisting of an amino acid sequence selected from the group consisting of: SEQ ID NOS:1-27, 41, 42, 43, 45, 46, and 47, or a functional peptidomimetic thereof, linked to a diagnostic moiety. In addition, the invention provides an isolated MMP-9 selective substrate polypeptide consisting of an amino acid sequence selected from the group consisting of: SEQ ID NOS:28-35 and 44, or a functional peptidomimetic thereof, linked to a diagnostic moiety. The invention further provides an isolated MT1-MMP selective substrate polypeptide consisting of an amino acid sequence selected from the group consisting of: SEQ ID NOS:36-40 or a functional peptidomimetic thereof, linked to a diagnostic moiety.

As used herein, the term "diagnostic moiety" means a moiety that is detectable external to a subject to whom it is administered and, thus, is useful for performing a diagnostic study. A diagnostic study can be performed in vivo, in situ, or in vitro. For example, a diagnostic study can be performed in a subject, a tissue slice or biopsy sample, cell culture, or in a test tube. For such studies, a moiety such as a gamma ray emitting radio-nucleotide, for example, indium-111 or technetium-99, can be linked to an MT1-MMP, MMP-2, or MMP-9 selective substrate polypeptide of the invention. For in vivo diagnostic studies, this conjugate can be administered to a subject and detected using a solid scintillation detector. Similarly, a positron emitting radionucleotide such as carbon-11 or a paramagnetic spin label such as carbon-13 can be linked to an MT1-MMP, MMP-2, or MMP-9 selective substrate polypeptide of the invention and, following administration to a subject, the localization of the diagnostic moiety can be detected using positron emission transaxial tomography or magnetic resonance imaging, respectively (van Roggen et al., *Curr. Opin. Rheumatol.* 12:77-83 (2000); Stubbs et al., *Acta Oncol.* 38:845-853 (1999); Ikeda et al., *Topics Magn. Reson. Imaging* 10:143-151 (1999); Parker et al., *Topics Mangy. Reson. Imaging* 10:130-142 (1999)). Such methods, for example, can identify primary tumors as well as a metastatic lesions, which might not be detectable using other methods.

In addition, these methods can be used to detect inflammatory diseases or diseases of the CNS where MMP-MT1, MMP-2, or MMP-9 are involved.

A diagnostic moiety can also be, for example, a MRI contrast dye or a fluorescent agent. In one embodiment, the invention provides an isolated MT1-MMP, MMP-2, or MMP-9 selective substrate polypeptide of the invention described above where the diagnostic moiety is a quenched fluorophore, for example, a near-infrared fluorescence (NIRF) imaging probe. These biocompatible, optically quenched NIRF imaging probes can generate a strong NIRF signal after enzyme activation such as hydrolysis by a proteinase (Weissleder et al., *Nature Biotech.* 17:375-378 (1999), incorporated herein by reference). A NIRF imaging probe can be linked to a MT1-MMP, MMP-2, or MMP-9 selective substrate polypeptide of the invention in order to specifically target the NIRF imaging probe to a site of activity of these MMPs such as a tumor or a site of inflammation. The NIRF moiety linked to a selective substrate polypeptide of the invention can be used to define and measure a site of MMP activity, for example, this conjugate can be used to image a tumor.

A problem with diagnosis of tumors is that often tumors must be of a certain size before they can be detected using conventional imaging systems. The sensitivity of the NIRF imaging probe system is sufficient to allow detection of small tumors, for example tumors that are less than 300 micrometers in diameter. This can allow for earlier diagnosis of tumors which is known to be correlated with a more successful treatment outcome. In addition to the sensitivity of the NIRF imaging probe system, this system linked to a selective substrate polypeptide of the invention can result in high affinity targeting of the moiety to a tumor which can overcome signal to noise or background problems found with conventional imaging systems.

A diagnostic moiety linked to a MMP selective substrate polypeptide can be used to diagnose, predict, prevent, and monitor diseases involving these metalloproteinases. The selective substrate polypeptides of the invention can be used to detect active MMPs at a particular site in vivo, in situ or in vitro. These active MMPs can be more relevant in terms of diagnosis and treatment of MMP-associated diseases than other less active or non-active MMPs.

The selective substrate polypeptides of the invention can be used to profile the active MMP status of a particular site in vivo, in situ or in vitro. For example, a selective substrate polypeptide linked to a diganostic moiety can be used to detect the presence of a particular active MMP at different stages of a disease either in vivo or using tissue or other samples taken at various times during the course of a disease. For example, a MMP-2 selective substrate polypeptide of the invention linked to a moiety can be added to tumor samples taken at various stages of tumor progression to determine if the level of active MMP-2 changes during progression of the disease. This same procedure can also be performed with tumor samples obtained from different tumors from the same or different patients. In addition this procedure can be performed with MMP-9 and MT1-MMP selective substrate polypeptides to get a profile of active MMP patterns during the course of a particular disease. The presence of a particular active MMP or a profile of active MMPs can be used, for example, to determine the stage of tumor progression in a patient who first presents with a tumor. In addition, the course of the patients disease can be monitored over time, for example, the effectiveness of a certain treatment can be determined by assessing the active MMP or MMP profile before and after treatment.

The presence of a particular active MMP or a profile of active MMPs can be useful in the prognosis of a disease course. For example, a particular active MMP can be correlated with more aggressive disease progression and hence can indicate the need for a more aggressive treatment protocol. Alternatively, a particular active MMP can indicate a slow course of disease progression and hence a different or no treatment protocol. Correlations between the presence of certain proteins and disease progression have been shown in some diseases, for example, the over-expression of the her2-neu oncogene in tumors from breast tissue indicates a more aggressive disease progression. In addition, the presence of a particular active MMP or a profile of active MMPs can be useful in detecting a particular disease, for example, in cases where the presence of that MMP is predictive of a particular disease or the state of a particular disease. In some cases where a patient is predicted to be at risk for a certain disease, methods which target these MMPs, alone or in combination with other methods known in the art, can be implemented in order to prevent that disease.

The presence of a particular active MMP or a profile of active MMPs in a particular disease can be useful for early detection of a disease. For example, if a particular active MMP is present early in the course of a disease, and is not substantially present later in the disease, then this MMP can be used as an early marker for the disease. In some cases early detection of a disease can correlate to a better outcome for the patient. In addition, the presence of a particular active MMP or a profile of active MMPs in a particular disease can be useful for treatment of a disease. For example, a particular active MMP can be over-expressed in a disease and targeting that MMP with a drug or other therapy can result in an effective treatment for the disease.

In addition to diagnostic moieties, the selective substrate polypeptides of the invention can be linked to other moieties. These moieties will be targeted to the site of an active MMP through the selective substrate polypeptide. In another embodiment, a moiety useful in the invention is a therapeutic moiety. A therapeutic moiety can include, for example, a cytotoxic agent, including a chemotherapeutic agent or a radioactive agent, an anti-antigogenic agent, a pro-angiogenic agent, and an agent that promotes tissue repair. The invention provides, specific binding polypeptides and selective substrate polypeptides linked to a therapeutic moiety. Further, the invention provides an isolated MMP-2 selective substrate polypeptide consisting of an amino acid sequence selected from the group consisting of: SEQ ID NOS:1-27, 41, 42, 43, 45, 46, and 47, or a functional peptidomimetic thereof, linked to a therapeutic moiety. In addition, the invention provides an isolated MMP-9 selective substrate polypeptide consisting of an amino acid sequence selected from the group consisting of: SEQ ID NOS:28-35 and 44, or a functional peptidomimetic thereof, linked to a therapeutic moiety. The invention further provides an isolated MT1-MMP selective substrate polypeptide consisting of an amino acid sequence selected from the group consisting of: SEQ ID NOS:36-40 or a functional peptidomimetic thereof, linked to a therapeutic moiety.

In one embodiment, a moiety useful in the invention is a cytotoxic agent such as a chemotherapeutic agent or a radioactive agent. Therefore, the invention provides an isolated MT1-MMP, MMP-2, or MMP-9 selective substrate polypeptide of the invention described above where the therapeutic moiety is a cytotoxic agent. Cytotoxic agents can be used in the treatment of cancer as well as inflammatory and other diseases.

Cytotoxic chemotherapy or radiation therapy is the basis of the systemic treatment of disseminated malignant tumors. However, a limitation of the currently used cytotoxic agents is that these agents have a narrow therapeutic index. As such, the dose of these cytotoxic agents generally is limited by undesirable toxicity. However, coupling of a MT1-MMP, MMP-2, or MMP-9 selective substrate polypeptide of the invention to a cytotoxic agent can effectively increase the concentration of the cytotoxic agent at a site of MMP activity, such as a tumor, and reduce side effects associated with the presence of the toxic agent in other tissues.

The invention provides a MT1-MMP, MMP-2, or MMP-9 selective substrate polypeptide of the invention as described above linked to one of a variety of chemotherapeutic agents, including, for example, anthracyclins, alkylating agents, vinca alkaloids, nucleotide analogs, cis-platinum, doxoribicin, methotrexate and mitomycin C. A chemotherapeutic agent useful in the invention can be, for example, an anthracyclin such as doxorubicin, which is a commonly used cancer chemotherapeutic agent and is useful for treating breast cancer (Sivam et al., *Cancer Res.* 55:2352-2356 (1995); Lau et al., *Bioorg. Med. Chem.* 3:1299-1304 (1995); Shih et al., *Cancer Immunol. Immunother.* 38:92-98 (1994); Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449-454 (eds. Steiner et al.; Birkhauser Verlag, 1992)), which can contribute to its effectiveness in treating cancer. Other anthracyclins, including idarubicin and daunorubicin, also can be linked to an MT1-MMP, MMP-2, or MMP-9 selective substrate polypeptide of the invention and delivered effectively to angiogenic vasculature (Rowland et al., *Cancer Immunol. Immunother.* 37:195-202 (1993); Aboud-Pirak et al., *Biochem. Pharmacol.* 38:641-648 (1989)).

A chemotherapeutic agent useful in the invention also can be an alkylating agent such as melphalan or chlorambucil (Rowland et al., supra, 1994; Smyth et al., *Immunol. Cell Biol.* 65:315-321 (1987)); or a vinca alkaloid such as vindesine or vinblastine (Aboud-Pirak et al., supra, 1989; Starling et al., *Bioconj. Chem.* 3:315-322 (1992)); or an antimetabolite such as 5-fluorouracil, 5-fluorouridine or a derivative thereof (Krauer et al., *Cancer Res.* 52:132-137 (1992); Henn et al., *J. Med. Chem.* 36:1570-1579 (1993)). Other chemotherapeutic agents, including cis-platinum (Schechter et al., *Int. J. Cancer* 48:167-172 (1991)), methotrexate (Sheller et al., *J. Biol. Resp. Mod.* 7:608-618 (1988); Fitzpatrick and Garnett, *Anticancer Drug Des.* 10:11-24 (1995)) or mitomycin-C (Dillman et al., *Mol. Biother.* 1:250-255 (1989)) also can be therapeutically effective when linked with an MT1-MMP, MMP-2, or MMP-9 selective substrate polypeptide of the invention.

In another embodiment, a MT1-MMP, MMP-2, or MMP-9 selective substrate polypeptide of the invention can be linked to an inactive therapeutic moiety which is activated upon hydrolysis of the selective substrate polypeptide. For example, the primary amine of the chemotherapeutic agent doxorubicin can be linked to the COOH-terminal carboxyl of a MT1-MMP, MMP-2, or MMP-9 selective substrate polypeptide of the invention thus inactivating doxorubicin. This inactivated form of doxorubicin is called a prodrug. Hydrolysis of the MT1-MMP, MMP-2, or MMP-9 selective substrate polypeptide can activate the doxorubicin prodrug to a cytotoxic form. In this way, the doxorubicin prodrug is converted to the active drug specifically at the site of activity of the linked selective substrate polypeptide, for example a tumor. This can result in less side effects and greater concentration of active doxorubicin at the desired site. The use of doxorubicin prodrugs linked to polypeptide carriers has been demonstrated using a polypeptide specific for the serine protease prostate-specific antigen (PSA) (Denmeade et al., *Cancer Res.* 58:2537-2540 (1998), and DeFeo et al., *Nature Med.* 6:1248-1252 (2000) incorporated herein by reference).

In another embodiment, a therapeutic moiety can be an anti-angiogenic agent, for example an anti-angiogenic polypeptide. The invention provides an isolated MT1-MMP, MMP-2, or MMP-9 selective substrate polypeptide of the invention described above where the therapeutic moiety is an anti-angiogenic agent. As used herein, the term "antiangiogenic polypeptide" means a polypeptide that functions to inhibit the development of blood vessels. An antiangiogenic polypeptide useful in the invention can be, for example, thrombospondin (Dawson et al., *Mol. Pharmacol.* 55:332-338 (1999)); angiostatin (O'Reilly et al., *Cell* 79:315-328 (1994)); endostatin (O'Reilly et al., *Cell* 88:277-285 (1997); Blezinger et al., *Nature Biotechn.* 17:343-348 (1999)); or pigment epithelium-derived factor (Dawson et al., *Science* 285:245-248 (1999)). An antiangiogenic polypeptide useful in the invention also can be, for example, a cleaved or active form of the serpin antithrombin (O'Reilly et al., *Science* 285:1926-1928 (1999). These and other polypeptides with activity in inhibiting the growth of blood vessels can be antiangiogenic polypeptides useful in the invention. Anti-angiogenic agents that can be linked to a selective substrate polypeptide include, for example, Kringle 5 of plasminogen, angiostatin, endostatin, tissue inhibitors of metalloproteinases, thalidomide, kinase antagonists, integrin antagonists (such as RGD mimics), and antagonists of urokinase.

In another embodiment, a therapeutic moiety is a proangiogenic agent or an agent that promotes tissue repair. The invention provides an isolated MT1-MMP, MMP-2, or MMP-9 selective substrate polypeptide of the invention described above where the therapeutic moiety is a pro-apoptotic agent or an agent that promotes tissue repair. As used herein, the term "proangiogenic agent" means a molecule that functions to stimulate the development of new blood vessels. Such angiogenesis-based therapy can be used, for example, to treat ischemic heart disease such as chronic myocardial ischemia or acute myocardial infarction (Ware and Simons, *Nature Med.* 3:158-164 (1997)). Many patients with severe vascular disease that are not candidates for mechanical revascularization can benefit from angiogenesis-based therapy, including those patients with occlusion of vessels too small to be bypassed, those without conduits, and those who are not surgical candidates because of concomitant disease (Miller and Abrams, *Gen. Engin. News* 18:1 (1998)).

A proangiogenic agent useful in the invention can be a growth factor or cytokine that induces or promotes angiogenesis by stimulating endothelial cell growth or migration, for example, vascular endothelial growth factor (VEGF), also known as vascular permeability factor (VPF). This growth factor, which is a key regulator of angiogenesis, stimulates endothelial cell proliferation and increases endothelial permeability without similar stimulation of smooth muscle cells. (Dvorak et al., *Am. J. Pathol.* 146:1029-1039 (1995); Thomas et al., *J. Biol. Chem.* 271:603-606 (1996); Olofsson et al., *Proc. Natl. Acad. Sci., USA* 93:2576-2581 (1996); and Joukov et al., *EMBO J.* 15:290-298 (1996); Harada et al., *Am. J. Physiol.* 270:H1791-H1802 (1996); *J. Am. Coll. Cardiol.* 29:1371-1379 (1997)). Thus, a proangiogenic agent useful in the invention can be, for example, a recombinant 165 amino acid isoform of VEGF, designated rhVEGF, developed by Genentech; a nucleic acid molecule encoding the 121 amino acid isoform of VEGF (BioByPass™; GenVec/Parke Davis); or a nucleic acid encoding VEGF-2 (Vascular Genetics, Inc.). See, for example, Miller and Abrams, supra, 1998.

A pro-angiogenic agent also can be a member of the fibroblast growth factor (FGF) family such as FGF-1 (acidic), FGF-2 (basic), FGF-4 or FGF-5, and in particular, FGF-2 (Slavin et al., *Cell Biol. Int.* 19:431-444 (1995); Folkman and Shing, *J. Biol. Chem.* 267:10931-10934 (1992)). A fibroblast growth factor useful in a conjugate or method of the invention can be, for example, FIBLAST® (trafermin), a recombinant form of FGF-2 being developed by Scios, Inc. (Mountain View, Calif.) and Wyeth Ayerst Laboratories (Radnor, Pa.), or GENERX™, or an adenoviral gene therapy vector encoding FGF-4 developed by Collateral Therapeutics (San Diego, Calif.) and Schering A G (Miller and Abrams, supra, 1998).

Additional pro-angiogenic agents useful in the invention include angiopoietin-1, a factor that signals through the endothelial cell-specific Tie2 receptor tyrosine kinase (Davis et al., *Cell* 87:1161-1169 (1996)). Like vascular endothelial growth factor, angiopoietin-1 is essential for normal vascular development, and its overexpression leads to increased angiogenesis (Suri et al., *Cell* 87:1171-1180 (1996)).

The invention also provides a MT1-MMP, MMP-2, or MMP-9 selective substrate polypeptide linked to an agent that promotes tissue repair since, during the wound healing process, angiogenesis is beneficial. Exemplary agents that promote tissue repair useful in the invention include insulin-like growth factor, platelet derived growth factor, and other wound healing growth factors (Eming et al., *Br. J. Plast. Surgery* 50:491-500 (1997); and Braddock et al., *Int. J. Dermatol.* 38:808-817 (1999)).

A pro-angiogenic agent or agent that promotes tissue repair can be delivered, for example, as a protein as described in Harada et al., *J. Clin. Invest.* 94:623-630 (1994). Microspheres, for example, microspheres of 7 μm diameter to which an angiogenic factor such as bFGF is reversibly adsorbed through $SO_3$ residues, also can be linked to a MT1-MMP, MMP-2, or MMP-9 selective substrate polypeptide of the invention to selectively deliver the microspheres to a site of MT1-MMP, MMP-2, or MMP-9 activity, such as the angiogenic vasculature. Such microspheres lodge in the peripheral microcirculation without interfering with total flow and are slowly released over a period of a week (Arras et al., *Nature Biotech.* 16:159-162 (1998); see, also, Tice and Staas, *Nature Biotech.* 16:134 (1998)). A single injection of a biodegradable microsphere can be used to deliver a pro-angiogenic agent or agent that promotes tissue repair, releasing the molecule over one or several months following the injection, with the rate and duration of drug release controlled by factors such as the polymer type and microparticle size (Maulding, *Controlled Release* 6:167-176 (1987); Tice and Tabibi, pages 315-339 in Kydonieus (Ed.), *Treatise on Controlled Drug Delivery* Marcel Dekker, New York (1992)). A gene therapy vector also can be linked to a MT1-MMP, MMP-2, or MMP-9 selective substrate polypeptide of the invention to deliver a proangiogenic factor or agent that promotes tissue repair (see, for example, Isner et al., *Lancet* 348:370-374 (1996); Giordano et al., *Nature Med.* 2:534-539 (1996)).

In another embodiment, a therapeutic moiety can be a pro-apoptotic polypeptide, which is characterized by the ability to preferentially disrupt mitochondrial membranes as compared to eukaryotic membranes and is highly toxic to the mammalian cell type to which it is targeted and internalized (Ellerby et al., *Nature Med.* 5:1032-1038 (1999)). The invention provides an isolated MT1-MMP, MMP-2, or MMP-9 selective substrate described above where the therapeutic moiety is a pro-apoptotic agent. A pro-apoptotic polypeptide useful in a conjugate of the invention typically is highly basic and can have a linear or cyclic structure; a particularly useful pro-apoptotic polypeptide has an amphipathic α-helical structure (U.S. Pat. No. 5,789,542; Javadpour et al., *J. Med. Chem.* 39:3107-3113 (1996); and Blondelle and Houghten, *Biochem.* 31: 12688-12694 (1992)). A pro-apoptotic polypeptide can be a naturally occurring antimicrobial polypeptide such as a gramicidin, magainin, mellitin, defensin and cecropin, or an analog of a naturally occurring polypeptide, especially an analog that retains or enhances amphipathicity (Maloy and Kari, *Biopolymers* 37:105-122 (1995); Alvarez-Bravo et al., *Biochem. J.* 302:535-538 (1994); Bessalle et al., *FEBS* 274:151-155 (1990); and Blondelle and Houghten in Bristol (Ed.), *Annual Reports in Medicinal Chemistry* pages 159-168 Academic Press, San Diego).

In one embodiment, a pro-apoptotic polypeptide useful in the invention has a structure in which polar and non-polar amino acid residues are aligned to form an amphipathic helix, which is an α-helix in which the hydrophobic amino acid residues are predominantly on one face and the hydrophilic residues predominantly on the opposite face (Saberwal et al., *Biochim. Biophys. Acta* 1197:109-131 (1994); Maloy et al., *Biopolymers* 37:105-122 (1995)). In an amphipathic α-helix, there generally are an equivalent number of polar and nonpolar residues within the amphipathic domain and a sufficient number of basic residues to give the polypeptide an overall positive charge at neutral pH (Saberwal et al., *Biochim. Biophys. Acta* 1197:109-131 (1994)). One skilled in the art understands that helix-promoting amino acids such as leucine and alanine can be advantageously included in a pro-apoptotic polypeptide of the invention (see, for example, Creighton, supra, 1984).

A variety of polypeptides having an amphipathic α-helical structure are well known in the art and can be useful as a pro-apoptotic polypeptide when linked to a MT1-MMP, MMP-2, or MMP-9 selective substrate polypeptide of the invention. Such amphipathic pro-apoptotic polypeptides include synthetic, minimalist polypeptides based on a heptad building block scheme in which repetitive heptads are composed of repetitive trimers with an additional residue. These synthetic polypeptides include, for example, polypeptides of the general formula $[(X_1X_2X_2)(X_1X_2X_2)X_1]_n$ or $[(X_1X_2X_2)X_1(X_1X_2X_2)]_n$, where $X_1$ is a polar residue, $X_2$ is a nonpolar residue; and n is 2 or 3 (see Javadpour et al., supra, 1996). One skilled in the art understands that additional polypeptides having an amphipathic α-helical structure also are known in the art and useful in the invention (see, for example, U.S. Pat. No. 5,789,542 to McLaughlin and Becker).

In another embodiment, a therapeutic moiety can be an anti-inflammatory agent for the treatment of an inflammatory disease mediated by an MMP. Anti-inflammatory agents include, for example, cyclooxygenase antagonists, ICAM antagonists (including antibodies), LFA-1 antagonists, steroids such as dexamethasone, PPARαantagonists, and hypoestoxide. In addition, a therapeutic moiety useful in the invention can be a growth factor, such a nerve growth factor (NGF) or brain derived growth factor (BDNF) for the treatment of a disease of the nervous system mediated by an MMP. Furthermore, a therapeutic moiety useful in the invention can be an agonist or antagonist for a cellular receptor including integrins, G-protein-coupled receptors, receptor tyrosine kinases, such as the Eph family, growth factor receptors such as EGF and insulin receptors, death receptors such as TRAF, as well as agonists and antagonists for molecules including ion channels and enzymes.

In yet another embodiment, a moiety is a physical, chemical or biological material such as a liposome, microcapsule, micropump or other chambered microdevice useful as a drug delivery system. The invention provides an isolated MT1-MMP, MMP-2, or MMP-9 selective substrate described above where the therapeutic moiety is a liposome or microdevice. Generally, such microdevices should be nontoxic and, if desired, biodegradable. Various moieties, including microcapsules, which can contain an agent, and methods for linking a moiety, including a chambered microdevice, to a MT1-MMP, MMP-2, or MMP-9 selective substrate polypeptide of the invention are well known in the art and commercially available (see, for example, "Remington's Pharmaceutical Sciences" 18th ed. (Mack Publishing Co. 1990), chapters 89-91; Harlow and Lane, *Antibodies: A laboratory manual* (Cold Spring Harbor Laboratory Press 1988); see, also, Hermanson, supra, 1996).

One skilled in the art understands that one or more additional components can be included, if desired, as part of the selective substrate polypeptide-moiety conjugate, without adversely affecting the ability of the MT1-MMP, MMP-2, or MMP-9 selective substrate polypeptide to bind MT1-MMP, MMP-2 or MMP-9 within a site of MMP activity without effecting the activity of the therapeutic agent. For example, in some cases, it can be desirable to utilize an oligopolypeptide spacer between a MT1-MMP, MMP-2, or MMP-9 selective substrate polypeptide and a therapeutic moiety (Fitzpatrick and Garnett, *Anticancer Drug Des.* 10:1-9 (1995)).

A polypeptide useful in the invention, such as a MT1-MMP, MMP-2, or MMP-9 selective substrate polypeptide or a specific binding polypeptide, can be synthesized in required quantities using routine methods of solid state polypeptide synthesis or can be purchased from commercial sources (for example, Anaspec; San Jose, Calif.) and the desired moiety linked to the polypeptide. Where a conjugate contains a polypeptide moiety and a MT1-MMP, MMP-2, or MMP-9 selective substrate polypeptide, the bifunctional polypeptide can be conveniently produced by routine polypeptide synthesis methods. Several other methods useful for linking a moiety to a MT1-MMP, MMP-2, or MMP-9 selective substrate polypeptide are known in the art, depending on the particular chemical characteristics of the molecule. For example, methods of linking haptens to carrier proteins as used routinely in the field of applied immunology (see, for example, Harlow and Lane, supra, 1988; Hermanson, supra, 1996).

The selective substrate polypeptides of the invention are hydrolyzed by MT1-MMP, MMP-2, or MMP-9 at the indicated positions resulting in the generation of polypeptide fragments. If a moiety is linked to the carboxyl-terminus of the selective substrate polypeptide, one skilled in the art can substitute a variation of the amino acid sequence at the amino terminus. In addition, if a moiety is linked to the amino-terminus of the selective substrate polypeptide, one having skill in the art can substitute a variation of the amino acid sequence at the carboxyl-terminus. Therefore, the invention provides carboxyl-terminal and amino-terminal fragments of the selective substrate polypeptides of the invention linked to a moiety.

Table III lists the sequences of the carboxyl-terminal fragments generated by cleavage of the selective substrate polypeptides of the invention by MT1-MMP, MMP-2, or MMP-9. The invention provides these carboxyl-terminal fragments linked to a moiety either alone or with any combination of amino acids bonded to its amino terminus. The invention provides for a moiety linked to an isolated polypeptide consisting of an amino acid sequence selected from the group consisting of SEQ ID NOS:48-70 where the moiety is linked to the isolated polypeptide at a position other than the amino terminus. Some of these sequences end with the residues threonine (T) and alanine (A) since the nucleotides coding for these residues were used in the construction of the hexamer library. One skilled in the art will understand that other nucleotides coding for other residues could be used alternatively.

Similarly, Table IV lists the sequences of the amino-terminal fragments generated by cleavage of the selective substrate polypeptides of the invention by MT1-MMP, MMP-2, or MMP-9. The invention provides these amino-terminal fragments linked to a moiety either alone or with any combination of amino acids bonded to its carboxyl terminus. The invention provides for a moiety linked to an isolated polypeptide consisting of an amino acid sequence selected from the group consisting of SEQ ID NOS:70-110 where the moiety is linked to the isolated polypeptide at a position other than the carboxyl terminus. The invention further provides for a moiety linked to an isolated polypeptide consisting of an amino acid sequence comprising (I/L)-X-X, $X_{Hy}$-X-X, or H-X-X where the moiety is linked to the isolated polypeptide at a position other than the carboxyl terminus.

TABLE III

| SEQ ID | P1' | P2' | 3' |
|---|---|---|---|
| 48 | I | T | A |
| 49 | Y | T | A |
| 50 | L | T | A |
| 51 | I | I | T |
| 52 | L | L | T |
| 53 | L | Y | P |
| 54 | L | L | T |
| 55 | L | K | T |
| 56 | I | D | T |
| 57 | P | P | T |
| 58 | L | Q | T |
| 59 | V | H | T |
| 60 | H | W | T |
| 61 | I | W | L |
| 62 | R | T | A |
| 63 | A | T | A |
| 64 | V | S | T |
| 65 | L | S | G |
| 66 | I | S | N |
| 67 | F | T | A |
| 68 | L | R | T |
| 69 | M | Y | T |
| 70 | I | R | T |

TABLE IV

| SEQ ID | | | P3 | P2 | P1 |
|---|---|---|---|---|---|
| 71 | L | R | L | A | A |
| 72 | E | S | L | A | Y |
| 73 | P | M | I | S | V |
| 74 | | S | L | H | S |
| 75 | S | D | I | R | M |
| 76 | F | N | L | Y | N |
| 77 | | Y | L | Q | V |
| 78 | | | I | V | N |
| 79 | V | G | L | I | A |
| 80 | R | S | L | S | R |
| 81 | N | R | Y | S | S |
| 82 | G | A | V | S | W |
| 83 | A | N | I | S | D |
| 84 | W | T | S | S | W |
| 85 | T | I | L | S | L |
| 86 | | | F | N | S | M |
| 87 | H | M | H | K | A |
| 88 | | L | H | R | R |
| 89 | | M | H | S | R |

TABLE IV-continued

| SEQ ID | | | P3 | P2 | P1 |
|---|---|---|---|---|---|
| 90 | H | M | H | K | A |
| 91 | | R | H | L | G |
| 92 | | L | H | K | K |
| 93 | | | A | H | A | K |
| 94 | A | K | P | R | A |
| 95 | | | P | Y | V |
| 96 | E | Y | E | H | M |
| 97 | I | Y | L | G | W |
| 98 | K | G | P | R | Q |
| 99 | K | I | P | R | T |
| 100 | | | P | R | A |
| 101 | | | P | R | P |
| 102 | F | R | P | R | S |
| 103 | | | P | R | S |
| 104 | N | P | P | R | Y |
| 105 | S | V | P | R | H |
| 106 | | R | I | G | F |
| 107 | | R | A | M | H |
| 108 | | R | S | E | N |
| 109 | A | R | Y | R | W |
| 110 | L | I | S | H | S |

The MT1-MMP, MMP-2, and MMP-9 selective substrate polypeptides and specific binding polypeptides of the invention described herein linked to a moiety can be used in the methods of the invention.

As described previously, given the teachings and guidance herein, the descriptions with reference to MT1-MMP, MMP-2, or MMP-9 selective substrate polypeptides are similarly applicable to MT1-MMP, MMP-2, or MMP-9 specific binding polypeptides. Therefore, specific binding polypeptides can have substantially the same sequence as the selective binding polypeptides and can be attached to the same moieties such as diagnostic and therapeutic moieties. Moreover, the specific binding polypeptides also can be used in the methods described below analogously to the selective substrate polypeptides of the invention.

The invention provides a method of preferentially directing a moiety to a site of MT1-MMP, MMP-2, or MMP-9 activity, by administering to a subject an effective amount of an isolated MT1-MMP, MMP-2, or MMP-9 selective substrate polypeptide linked to the moiety. As used herein, the term "preferentially" when referring to directing a moiety to a site of MMP action, is intended to mean that the moiety will initially accumulate, or the selective substrate polypeptide containing the moiety will be hydrolyzed to a greater extent at a target site compared to non-target sites. For example, the moiety can be directed to a site of MMP activity, but not substantially directed to a different site of activity, such as a site of phosphatase activity.

An effective amount of a conjugate containing an isolated selective substrate polypeptide linked to a moiety is administered to the subject. An "effective amount" is the amount of the conjugate that produces a desired effect. An effective amount will depend, for example, on the moiety linked to the selective substrate polypeptide and on the intended use. An effective amount of a particular conjugate for a specific purpose can be determined using methods well known to those in the art. As used herein, the term "subject" means a vertebrate animal capable of expressing MT1-MMP, MMP-2 or MMP-9. The term subject generally refers to a mammalian subject, for example, a mouse, or a primate such as a human.

The invention provides a method of preferentially directing a moiety to a site of MMP-2 activity, by administering to a subject an effective amount of an isolated MMP-2 selective substrate polypeptide linked to the moiety, where the polypeptide contains an amino acid sequence selected from the group consisting of: SEQ ID NOS: 1-27, 41, 42, 43, 45, 46, and 47 or a functional peptidomimetic thereof. The moiety can be preferentially directed to a site of MMP activity in vivo, in situ or in vitro. For example, the moiety can be directed to a site of MMP activity in a subject, in a tissue slice or cell culture, or in a test tube. In addition, the invention provides a method of preferentially directing a moiety to a site of MMP-2 activity, by administering to a subject an effective amount of an isolated MMP-2 selective substrate polypeptide linked to the moiety, where the polypeptide contains an amino acid sequence selected from the group consisting of: SEQ ID NOS: 1-27, or a functional peptidomimetic thereof. The invention further provides a method of preferentially directing a moiety to a site of MMP-2 activity, by administering to a subject an effective amount of an isolated MMP-2 selective substrate polypeptide linked to the moiety, where the polypeptide comprises an amino acid sequence selected from the group consisting of: SEQ ID NOS:1, 2, 10, 11, 12, 13, 17, and 24.

The invention provides a method of preferentially directing a moiety to a site of MMP-9 activity, by administering to a subject an effective amount of an isolated MMP-9 selective substrate polypeptide linked to the moiety, where the polypeptide contains an amino acid sequence selected from the group consisting of: SEQ ID NOS:28-35 and 44, or a functional peptidomimetic thereof. In addition the invention provides a method of preferentially directing a moiety to a site of MMP-9 activity, by administering to a subject an effective amount of an isolated MMP-9 selective substrate polypeptide linked to the moiety, where the polypeptide contains an amino acid sequence selected from the group consisting of: SEQ ID NOS:28-35, or a functional peptidomimetic thereof. The invention further provides a method of preferentially directing a moiety to a site of MMP-9 activity, by administering to a subject an effective amount of an isolated MMP-9 selective substrate polypeptide linked to the moiety, where the polypeptide comprises the amino acid sequence SEQ ID NOS:28, 29, and 30.

The invention provides a method of preferentially directing a moiety to a site of MT1-MMP activity, by administering to a subject an effective amount of an isolated MT1-MMP selective substrate polypeptide linked to the moiety, where the polypeptide contains an amino acid sequence selected from the group consisting of: SEQ ID NOS:36, 37, 38, 39, and 40, or a functional peptidomimetic thereof.

The methods of the invention are useful for preferentially directing a moiety to a site of MT1-MMP, MMP-2, or MMP-9 activity for imaging such a site. Practicing the method includes the steps of administering to a subject a conjugate which contains an MT1-MMP, MMP-2, or MMP-9 selective substrate polypeptide linked to an imaging agent; and detecting the imaging agent, for example, using magnetic resonance imaging, thereby imaging the site of activity. A method of the invention can be useful for imaging, for example, angiogenic tumor vasculature. As used herein, the term "angiogenic vasculature" refers to proliferating blood vessels. Such angiogenic vessels are distinguishable from mature vasculature due, in part, to expression of unique endothelial cell surface markers, including the $\alpha_v\beta_3$ integrin (Brooks, *Cell* 79:1157-1164 (1994); WO 95/14714, Int. Filing Date Nov. 22, 1994) and receptors for angiogenic growth factors (Mustonen and Alitalo, *J. Cell Biol.* 129:895-898 (1995); Lappi, *Semin. Cancer Biol.* 6:279-288 (1995); Rehn et al., *Proc. Natl. Acad. Sci. USA* 98:1024-1029 (2001)).

In one embodiment, a method of the invention is useful for preferentially directing a moiety to angiogenic vasculature which is tumor vasculature. The term "tumor vasculature," as used herein, means angiogenic vasculature that supports the growth or maintenance of a tumor, which may be malignant or non-neoplastic. Like other angiogenic vessels, tumor vasculature can express unique endothelial cell surface markers. Moreover, tumor vasculature is histologically distinguishable from other blood vessels in that tumor vasculature generally is fenestrated (Folkman, *Nature Med.* 1:27-31 (1995); Rak et al., *Anticancer Drugs* 6:3-18 (1995)).

The methods of the invention also can be useful for preferentially directing a moiety to angiogenic vasculature that is not tumor vasculature or associated with neoplastic disease. Angiogenesis within the female reproductive tract, for example, is critical for normal reproduction and can be involved in pathogenesis of endometriosis (Donnez et al., *Human Reproduction* 13:1686-1690 (1998). Thus, a method of the invention can be useful in preferentially directing a moiety to non-tumor angiogenic vasculature such as endometrial vasculature. Neovascularization also has been described within the intima of human atherosclerotic lesions and, further, angiogenic inhibitors such as endostatin can reduce the intimal neovascularization and plaque growth evident in apolipoprotein E-deficient mice (Moulton et al., *Circulation* 99:1726-1732 (1999)). Thus, a method of the invention can be useful for preferentially directing a therapeutic moiety or imaging agent to angiogenic sites in atherosclerotic plaques. Unregulated angiogenesis also can be involved in other non-neoplastic diseases such as diabetic blindness and rheumatoid arthritis. Thus, a conjugate a selective substrate polypeptide of the invention can be useful for treating disorders involving tumor vasculature or other neovasculature such as the vasculature present in inflammatory or other disorders or the neovasculature present in regenerating or wounded tissue.

A method of the invention also can be useful for stimulating beneficial angiogenesis, such as in ischemia or tissue repair. A method of preferentially directing a moiety to stimulate angiogenesis relies on administering to a subject an isolated MT1-MMP, MMP-2, or MMP-9 selective substrate polypeptide linked to a proangiogenic agent or other agent that promotes tissue repair. A progangiogenic agent useful in the methods of the invention can be, for example, vascular endothelial growth factor or fibroblast growth factor. Other agents that promote tissue repair, including insulin-like growth factor and platelet derived growth factor, also can be useful when linked to an MMP-2/MMP-9 binding molecule as described further below.

The methods of the invention also can be useful for preferentially directing a moiety to other sites of activity of MT1-MMP, MMP-2, and MMP-9, such as, for example, the central nervous system, joints, vessel walls, skin, lungs, bone and kidneys, in pathological conditions.

For identification of a MT1-MMP, MMP-2, or MMP-9 binding molecule or selective substrate polypeptide, MT1-MMP, MMP-2 or MMP-9 can be prepared, for example, by purification of the proform of the enzyme from cell-conditioned media, or by recombinant methods. It is understood that a full-length form or appropriate fragment of the enzyme can be used when screening a molecule for binding or selective substrate activity. For example, purification of proMMP-2 can be accomplished using cell-conditioned media from skin explant, primary skin, gingival or synovial fibroblast or tumor cell sources. ProMMP-9 can be conveniently purified from U937 cell cultures or the supernatant from selectively degranulated neutrophils (Murphy and Crabbe, supra, 1995). Gelatinases can be partially separated from other matrix metalloproteinases by pretreatment of culture medium by chromatography on DEAE-Sepharose or Green A agarose, and the gelatinases purified by affinity chromatography using gelatin-Sepharose 4B or fast flow (Pharmacia; Piscataway, N.J.); other gelatin-binding proteins can be removed by a 1 M salt wash before elution of the gelatinases by 10% (v/v) dimethyl sulfoxide. In order to separate MMP-2 from MMP-9, concanavalin A (Con A)-Sepharose can be employed to selectively bind the glycosylated proMMP-9, followed by elution with methyl-α-D-mannoside (Murphy and Crabbe, supra, 1995). Methods of separating free proenzymes from proenzyme complexed with TIMP-1 or TIMP-2 also are known in the art, including selective elution from heparin Sepharose for separation of proMMP-2, and immunoaffinity chromatography using an anti-TIMP-1 antibody for separation of proMMP-9 (Kolkenbrock et al., *Eur. J. Biochem.* 198:775 (1991); Ward et al., *Biochem. J.* 278:179 (1991)). Activation of proMMP-2 or proMMP-9 can be accomplished by treatment with 4-aminophenylmercuric acetate (APMA). Activation can be followed by enzyme assay or SDS-PAGE which will show cleavage of the 72 kDa MMP-2 proenzyme to the 66 kDa active form, or cleavage of the 92 kDa MMP-9 proenzyme to the 65 kDa active form (Sorsa et al., *J. Biol. Chem.* 272: 21067-21074 (1997)).

Recombinant MT1-MMP, MMP-2, or MMP-9 also can be useful in the invention. Recombinant MT1-MMP, MMP-2 or MMP-9, such as recombinant human or murine forms can be prepared, for example, in baculovirus-infected insect cells or eukaryotic cells as described in the art (George et al., *Protein Expr. Purif.* 10:154-161 (1997); Masure et al., *Eur. J. Biochem.* 244:21-30 (1997); Fridman et al., *Biochem J.* 289 (pt 2): 411-416 (1993); see, also, (Collier et al., *J. Biol. Chem.* 263:6579 (1988); Wilhelm et al., *J. Biol. Chem.* 264:17213 (1989); Reponen et al., *J. Biol. Chem.* 267:7856 (1992); and Tanaka et al., *Biochem. Biophys. Res. Commun.* 190:732 (1993)). The skilled artisan readily appreciates that these and other routine biochemical and recombinant methods can be used to prepare isolated MT1-MMP, MMP-2 or MMP-9 useful in identifying a binding molecule or selective substrate polypeptide.

Libraries that can be screened for additional MT1-MMP, MMP-2 or MMP-9 binding molecules or selective substrate polypeptides include polypeptide, peptidomimetic, nucleic acid, phage display and chemical libraries. Methods of producing libraries containing diverse populations of various types of molecules such as peptides, peptoids and peptidomimetics are well known in the art, and numerous libraries are commercially available (see, for example, Ecker and Crooke, *Biotechnology* 13:351-360 (1995), and Blondelle et al., *Trends Anal. Chem.* 14:83-92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861, and Gordon et al., *J. Med. Chem.* 37:1385-1401 (1994)).

A library of molecules can be produced, for example, by constructing a cDNA expression library from mRNA collected from a cell, tissue, organ or organism of interest. Methods for producing such libraries are well known in the art (see, for example, Sambrook et al., *Molecular Cloning: A Laboratory Manual* (Cold Spring Harbor Laboratory Press 1989), which is incorporated herein by reference).

The molecules of a library can be tagged to facilitate identification of a MT1-MMP, MMP-2, or MMP-9 binding molecule or selective substrate polypeptide. Such a tag is a physical, chemical or biological moiety such as a plastic microbead, an oligonucleotide or a bacteriophage, respectively, that is linked to a molecule of the library. Methods for tagging a molecule are well known in the art (Hermanson, *Bioconjugate Techniques* (Academic Press 1996)).

In order to identify a MT1-MMP, MMP-2 or MMP-9 selective substrate peptidomimetic, libraries of potential peptidomimetics can be screened for binding activity using an in vitro binding assay as are well known in the art. The Cambridge Structural Database, for example, contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as a MT1-MMP, MMP-2 or MMP-9 selective substrate, as well as potential geometrical and chemical complementarity to these metalloproteinases bound by a polypeptide. Where no crystal structure of the substrate polypeptide or the target metalloproteinase is available, a structure can be generated using, for example, the program CONCORD (Rusinko et al., *J. Chem. Inf. Comput. Sci.* 29:251 (1989)). Another database, the Available Chemicals Directory (Molecular Design Limited, glbatimInformations Systems; San Leandro Calif.), contains about 100,000 compounds that are commercially available and also can be searched to identify a peptidomimetic of a MT1-MMP, MMP-2 or MMP-9 selective substrate polypeptide. A functional peptidomimetic can have higher, lower, or about the same functional activity as the polypeptide that it is mimicking.

When administered to a subject, a conjugate comprising an MT1-MMP, MMP-2, or MMP-9 selective substrate polypeptide and a moiety can be administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain a physiologically acceptable compound that acts, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the conjugate. If desired, the pharmaceutical composition also can contain in addition to the conjugate a second active agent such as a therapeutic agent or other therapeutic agent.

One skilled in the art understands that a conjugate containing a MT1-MMP, MMP-2, or MMP-9 selective substrate polypeptide can be administered to a subject by various routes including, for example, orally or parenterally, such as intravenously, or by injection or intubation. In performing a therapeutic or imaging method as disclosed herein, an effective amount of a conjugate comprising an MT1-MMP, MMP-2, or MMP-9 selective substrate polypeptide must be administered to the subject. An effective amount is the amount of the conjugate that produces a desired effect and depends, for example, on the moiety linked to the MT1-MMP, MMP-2, or MMP-9 selective substrate polypeptide and on the intended use. For example, a smaller amount of a conjugate administered for imaging angiogenic vasculature can be required as compared to the amount of conjugate administered for therapeutic purposes.

The route of administration of an MT1-MMP, MMP-2, or MMP-9 selective substrate polypeptide will depend, in part, on the chemical structure of the MT1-MMP, MMP-2, or MMP-9 selective substrate polypeptide. Some polypeptides, for example, are not particularly useful when administered orally because they can be degraded in the digestive tract. However, methods for chemically modifying an MT1-MMP, MMP-2, or MMP-9 selective substrate polypeptide to render it less susceptible to degradation by endogenous proteases or more absorbable through the alimentary tract are well known in the art (see, for example, Blondelle et al., supra, 1995; Ecker and Crooke, supra, 1995; Goodman and Ro, supra, 1995). In addition, methods for preparing libraries of polypeptide analogs such as polypeptides containing D-amino acids; peptidomimetics consisting of organic molecules that mimic the structure of a polypeptide; or peptoids such as vinylogous peptoids, have been previously described above and can be used to identify MT1-MMP, MMP-2, or MMP-9 selective substrate polypeptides suitable for oral administration to a subject.

EXAMPLE I

Construction of the Phase Library

The fUSE5 polyvalent phage display vector was modified to express random hexamers at the amino terminus of the gene111 protein, and an octapeptide FLAG epitope at the amino-terminal end of the random hexamers. The FLAG epitope was engineered at the N-terminus of the geneIII protein by annealing oligonucleotides CCGGGTTTGTCGTCGTCGTCTTTGTAGTCGGTAC (SEQ ID NO:111) and CGACTACAAAGACGACGACGA-CAAAC (SEQ ID NO:112) and ligating them into fUSE5 at the Kpn I and Xba I restriction sites. The random hexamers were generated by PCR extension of the template oligonucleotide GGGGAGGCCGACGTGGCCGTCATCAG-GCGGCTCAGGC (NNK)$_6$ACGGCCTCTGGGGC CGAAAC (SEQ ID NO:113), where N is any nucleotide and K is either G or T. The template oligonucleotide also encodes an SGGSG (SEQ ID NO:114) linker position in between the FLAG epitope and the random hexamer. A primer oligonucleotide AATTTCTAGTTTCGGCCCCAGAGGC (SEQ ID NO:115) and the template oligonucleotide were mixed and heated at 65° C. for two minutes. The heating block was then cooled to 40° C. at room temperature to allow annealing of the extension oligonucleotide. Elongation of the template oligonucleotide was performed using Sequenase (USB). The final cDNA product was precipitated with ethanol, re-suspended in water and digested with Sfi I. The DNA insert and fUSE5 were mixed and ligated at a 5:1 molar ratio and electroporated into E. coli MC1061(F-). Several phage were selected for sequencing to confirm the random sequence of the inserts and the proper coding frame. The complexity of the library was 2.4×10$^8$ independent transformants giving a 75% confidence that each of the 6.4×10$^7$ possible random hexamer sequences are represented in the library. Sequencing of phage confirmed the randomness of the hexamer insert. Under the selection conditions, greater than 95% of phage could be immunodepleted using an anti-FLAG antibody (data not shown).

EXAMPLE II

MMP-2 Selective Substrate Polypeptide

The substrate phage library used for MMP-2 selective substrate polypeptide detection had 2.4×10$^8$ individual sequences, ensuring with 75% confidence that all possible sequences are represented.

Recombinant MMP-2 was generated in a manner similar to that we have previously reported for MMP-9 (Kridel, et al., J. Biol. Chem. 276:20572-20578 (2001)). Briefly, the cDNA encoding the catalytic domain of MMP-2 was generated by PCR and cloned into the pCDNA3 expression vector (Invitrogen) and used to transfect HEK 293 cells. Individual antibiotic resistant clones were isolated with cloning rings, expanded, and then screened by RT-PCR and zymography. The catalytic domains of MMP-2 and 9 were purified from the conditioned medium by gelatin-Sepharose chromatography. We also employed an additional purification by ion exchange on Q-Sepharose to obtain greater purity. Fractions containing MMP-2 or 9 were concentrated in a dialysis bag against Aquacide II (Calbiochem). The purity of both enzymes was greater than 90% judging by silver stained acrylamide gels. The purified zymogens of MMP-2 and 9 were stored at −70° C. at concentrations ranging from 0.4-1.3 mg/ml.

MMPs were activated by 2 mM p-Aminophenylmercuric Acetate (APMA) at room temperature. APMA was used to activate the two MMPs to avoid the inclusion of additional contaminating proteases in our phage selections. After activation, the activities of MMP-2 and MMP-9 were titrated using the hydroxamate inhibitor Ilomastat as previously described (Kridel, supra). The active sites of full length MMP-13 and MMP-7 were titrated with human TIMP-2. Briefly, 5-15 nM of each protease was pre-incubated with a range of TIMP-2 for five hours at room temperature. Residual MMP-13 activity was monitored by cleavage of MCA-Pro-Cha-Gly-Nva-His-Ala-Dpa-NH$_2$ (SEQ ID NO:116) (Calbiochem). Residual MMP-7 activity was monitored by cleavage of MCA-Pro-Leu-Gly-Leu-Dpa-Ala-Arg-NH$_2$ (SEQ ID NO:117) (Calbiochem).

Selection of MMP-2 Substrates From the Phage Library

The substrate phage library (2×10$^{10}$ phage) was incubated with 2.5 μg/ml of MMP-2 in 50 mM Tris, pH 7.4, 100 mM NaCl, 10 mM CaCl$_2$, 0.05% Brij-35, and 0.05% BSA for 1 hour at 37° C. A control reaction was performed without protease. The cleaved phage were separated from the non-cleaved phage by immuno-depletion. 100 μg of an anti-FLAG monoclonal antibody (Sigma) was added to the phage samples and then incubated for 18 hours with rocking at 4° C. The phage-antibody complexes were twice precipitated by the addition of 100 μl Pansorbin (Calbiochem). The cleaved phage remaining in the supernatant were amplified using K91 E. coli, and were then used for one additional round of substrate selection.

Monitoring Phage Hydrolysis by ELISA

Figure 2:
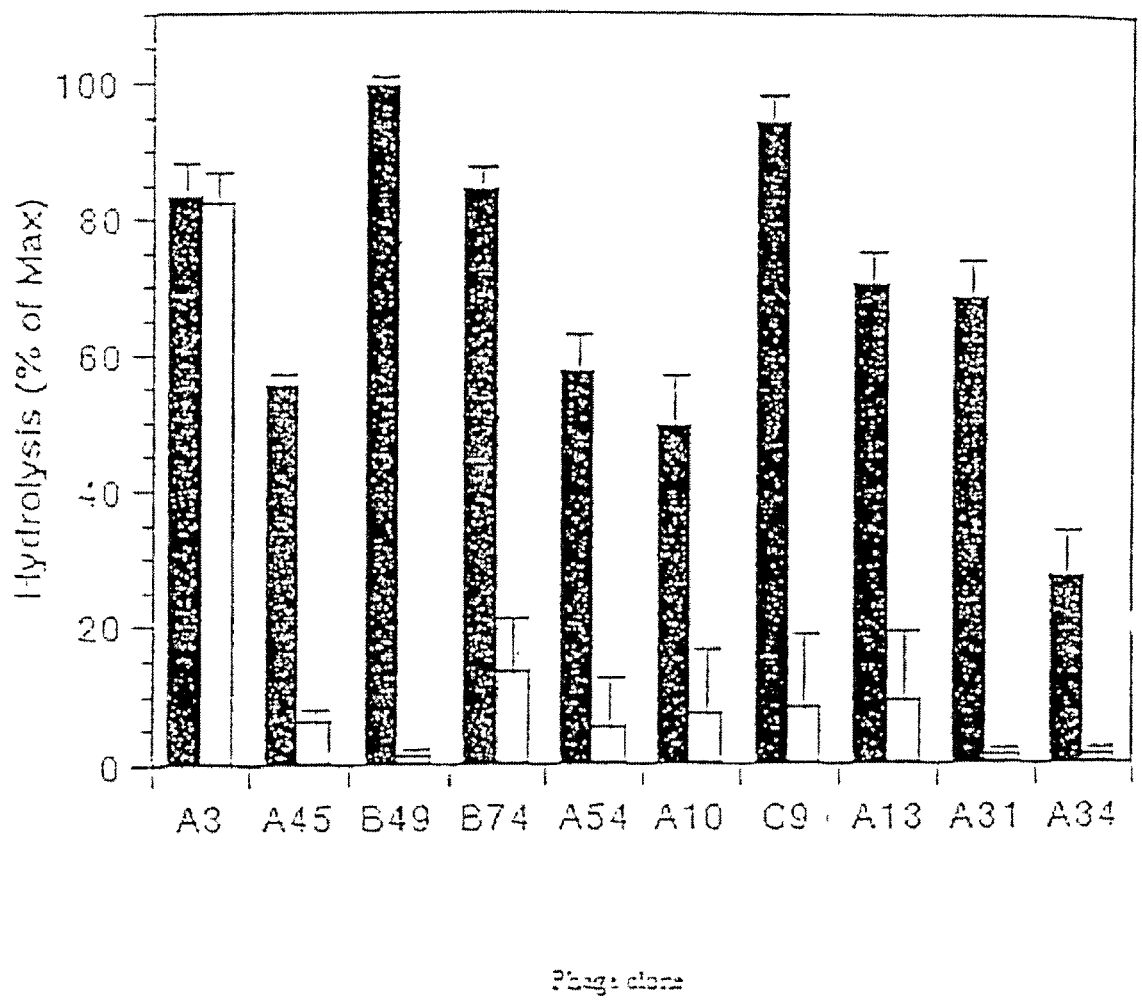
FIG. 2 shows the selectivity of phage substrates for MMP-2 or MMP-9. The ability of MMP-2 (dark bars) and MMP-9 (open bars) to cleave substrate selected from a phage library were compared using the phage ELISA procedure described in Example II. Immobilized phage were cleaved with MMP-2 or MMP-9. The extent of cleavage within the phage insert was assessed by measuring the release of the FLAG epitope. Results are presented as the percentage of hydrolysis compared to non-treated control phage.

Hydrolysis of individual phage substrates was measured using a modified ELISA that we have previously described (Kridel, supra). Briefly, phage from overnight cultures were captured into microtiter plates coated with anti-M13 antibody (Pharmacia, 2.5 μg/ml). The captured phage were incubated with MMP-2 (2.5 μg/ml) in Incubation Buffer (50 mM Tris, pH 7.5, 100 mM NaCl, 10 mM CaCl$_2$, 0.05% BSA, 0.05% Brij-35, 50 μM ZnCl$_2$) for 2 hours at, 37° C. Control wells lacked protease. Following hydrolysis and extensive washing, anti-FLAG polyclonal antibody (1.8 μg/ml in TBS-T with 1 mg/ml BSA) was added to the wells and incubated for 1 hr. Following additional washing, the level of bound anti-FLAG antibody was quantified with an HRP-conjugated goat anti-rabbit IgG antibody (BioRad) followed by detection at 490 nm. The extent of hydrolysis of each phage was calculated by the ratio of the O.D. at 490 nm of the protease-treated samples versus samples lacking protease. The rate of hydrolysis of a set of representative phage substrates by MMP-2 and MMP-9 is shown in FIG. 2. The position of scissile bonds within the polypeptide substrates was mapped using the procedure in Example V.

Quantifying the Kinetics Parameters of Peptide Hydrolysis

Figure 4:
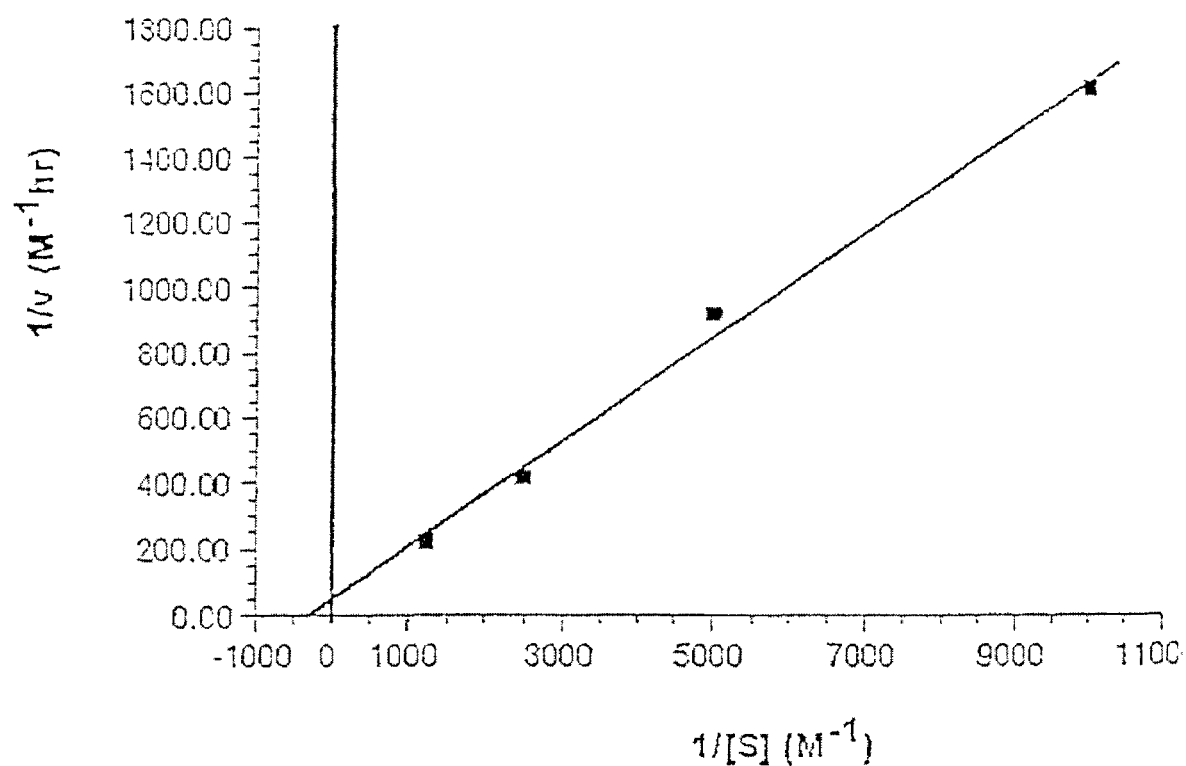
FIG. 4 shows a double reciprocal plot of B74 polypeptide cleaved by MMP-2. The initial velocity of B74 hydrolysis was measured by incubating MMP-2 with 100, 200, 400, and 800 μM of polypeptide. The double reciprocal plot of 1/[S] vs. 1/V was then generated and used to derive an equation from the best-fit line. The value of $K_m$ is equal to $-1/X$-intercept and the value of $k_{cat}$ is equal to Vmax/[E] [S].

The kinetic parameters of substrate hydrolysis were measured using a fluorescamine incorporation assay that has been previously described (Ding et al., *PNAS*, 92:7627-7631 (1995); Coombs et al., *Chem. and Biol.* 5:475-488 (1998); Fields et al., *J. Biol. Chem.*, 262:6221-6226 (1987); Netzel-Arnett., et al. *J. Biol. Chem.*, 266:6747-6755 (1991)). Briefly, MMP-2, MMP-9, MMP-7, or MMP-13 were incubated with individual peptide substrates at concentrations ranging from 100-800 μM in 50 mM Tris, pH 7.5, 100 mM NaCl, 10 mM CaCl$_2$, 50 μM ZnCl$_2$. At selected time points the reactions were stopped by the addition of 1,10-phenanthroline. Peptide hydrolysis was determined by the addition of fluorescamine followed by detection at $\lambda_{ex}$ 355 nm and $\lambda_{em}$ 460 nm. The data were transformed to double reciprocal plots (1/[S] vs 1/$v_i$) to determine K$_m$ and k$_{cat}$. For some substrates, K$_m$ and k$_{cat}$ could not be determined individually, but the specificity constant, k$_{cat}$/K$_m$, was derived by the equation: k$_{cat}$/K$_m$=$v_i$/(E$_0$)(S$_0$), and with the assumption that (S) is significantly lower than the K$_m$ (Netzel-Arnett, supra). A double reciprocal plot of the hydrolysis of peptide B 74 is shown as a representative plot (FIG. 4).

Assessing Cleavage of Recombinant Eph Receptors by MMP-2 and MMP-9

Recombinant fusion proteins between EphB1, EphB2 and the Fc domain of IgG were purchased from R&D Systems Inc. In these constructs, the extracellular domain of rat EphB1 (amino acid residues 1-538) and mouse EphB2 (amino acid residues 1-548) are fused to the Fc region of human IgG via a short polypeptide linker. The fusion proteins (1.8 μM) were incubated for 4 hours at 37° C. with 280 nM of either MMP-2 or MMP-9. Following incubation, samples were resolved by 10% SDS-PAGE, and samples were visualized by Coomassie staining. The N-terminus of the cleaved Eph B1 was determined by automated Edman degradation of protein blotted to PVDF membranes.

Several experiments were conducted to gain a better understanding of the structural basis for the selectivity of the substrates in Table I. Two hypotheses were tested. The first centered on the fact that several substrates do not contain a Pro at the P$_3$ position. Since this residue is frequently found in substrates for other MMPs, and is also present at this position in some of the substrates, we reasoned that its absence may be a defining feature of this set of selective substrates. To test this hypotheses, variants of three peptides were synthesized to contain a Pro at P$_3$, and their hydrolysis by each MMP was measured. Although the inclusion of Pro at P$_3$ increased the k$_{cat}$/K$_m$ ratio for MMP-9 between three and eleven-fold, the proline-containing peptides remained better substrates for MMP-2 (data not shown). Consequently, the absence of Pro at the P$_3$ position is not the only determinant in the selectivity of these substrates.

The second hypothesis was based on the presence of Arg at the P$_2$ position. Since Arg is rarely present at P$_2$ in the substrates selected for MMP-2, but is often present in MMP-9 selective substrates (Table I), we hypothesized that substitution of Arg into P$_2$ might shift selectivity away from MMP-2 and toward MMP-9. Indeed, in the three peptides tested, B74, A13 and C9, the substitution of Arg into the P2 position increased hydrolysis by MMP-9. This substitution also decreased hydrolysis by MMP-2. In combination, these effects switch the selectivity ratio of the mutated peptides. These findings underscore the significance of Arg at P$_2$ in facilitating substrate recognition by MMP-9, and also point to the important role of the S$_2$ subsite in distinguishing the activity of MMP-2 and MMP-9. Interestingly, the substitution of Arg at P$_2$ had minimal effects on the k$_{cat}$/K$_m$ ratio of MMP-7 or MMP-13, indicating that other features, that are still not understood, confer selectivity of these peptides for MMP-2 over MMP-7 and MMP-13.

Selective hydrolysis of a protein substrate containing the S-X-L Motif

One use from this study would be to use the substrate recognition profiles obtained from substrate phage, and other substrate profiling strategies, to generate hypotheses regarding physiologic substrates. As an initial step in this direction, we compared the ability of MMP-2 and MMP-9 to cleave Eph B1 and Eph B2, tyrosine kinase receptors that are responsible for cell-cell signaling in neuronal development. These proteins contain putative cleavage sites that correspond rather closely to the substrates selected from the phage library by MMP-2. There are two potential cleavage sites within Eph B1. The first motif contains the sequence is S-I-S-S-L-W (SEQ ID NO:118), which matches well with the X$_{Hy}$-S-X↓L (SEQ ID NO:119) motif. This motif is positioned within a predicted β-strand within a fibronectin repeat in Eph B1. A second potential cleavage site with a sequence of K-S-E-L (SEQ ID NO:120), is located in a ten residue linker between the membrane spanning segment and the second type III repeat of Eph B1. This sequence does not precisely match the motif of the substrates, but it does contain the core S-X-L motif. In the recombinant form of Eph B1 used here, this putative cleavage site is positioned in a short segment between the second fibronectin type III repeat, and the Fc domain of IgG. Eph B2 contains only a single putative cleavage site, with a sequence of is Y-I-S-D↓L-L (SEQ ID NO:121). This motif is positioned in a predicted β-strand in the second type III fibronectin repeat and it corresponds to the X$_{Hy}$-S-X↓L (SEQ ID NO:42) motif. EphB2 lacks the second predicted cleavage site, even though the recombinant protein contains an analogous linker.

Figure 3:
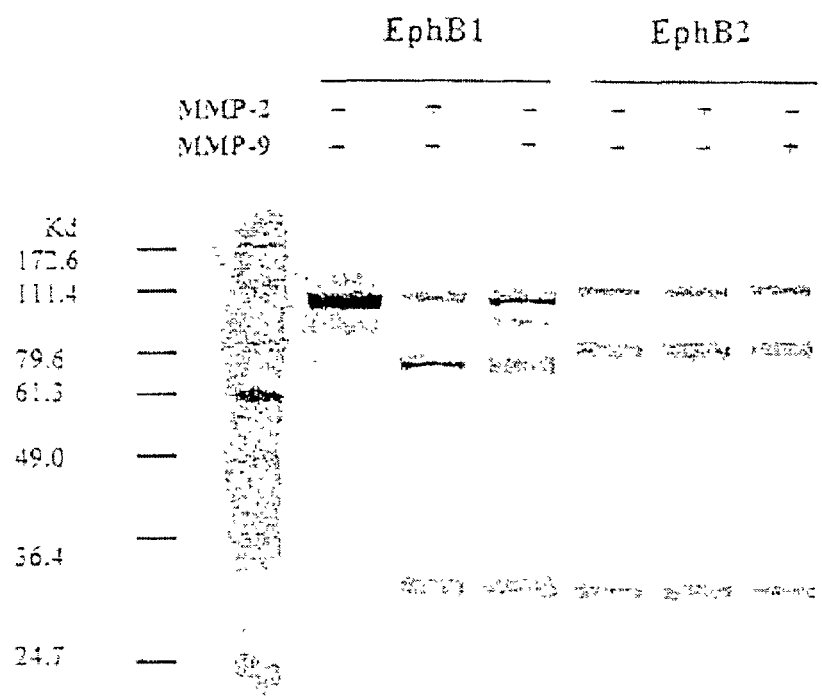
FIG. 3 shows the selective cleavage of the tyrosine kinase receptor EphB1 by MMP-2. An EphB1 or EphB2 fusion protein was incubated with MMP-2 or MMP-9. Samples were resolved by 10% SDS-PAGE, and the proteins were visualized by Coomassie blue staining.

The Eph B1 and Eph B2 fusion proteins were incubated with equimolar amounts (280 nM) of MMP-2 and MMP-9 for four hours. The extent of hydrolysis was gauged by SDS-PAGE (FIG. 3). The Eph B1-Fc fusion protein was almost quantitatively cleaved by MMP-2 (lane 2). The extent of cleavage by MMP-9 was far lower (lane 3). Neither protease cleaved the Eph B2 fusion protein. The site of hydrolysis within Eph B1 was determined by sequencing the N-terminus of one of the released fragments. The amino acid sequence of this fragment indicates that the protein was cleaved at the sequence D-D-Y-K-S-E ↓ L-R-E (SEQ ID NO:122), that is found within the ten residue linker of Eph B1. This is one of the predicted cleavage sites in EphB1. These findings illustrate that motifs found to be selective for MMP-2 by substrate phage display, can act as selective substrates within the context of whole proteins. This experiment also illustrates that the three dimensional conformation of the putative cleavage site will also control the extent of hydrolysis.

EXAMPLE III

MMP-9 Selective Substrate Polypeptides

Selection of peptide substrates for MMP-9

Optimal substrates were selected by exposing the phage library to a recombinant form of the catalytic domain of MMP-9 expressed in HEK 293 cells. The recombinant catalytic domain of MMP-9 was purified on gelatin-Sepharose followed by ion exchange chromatography. The protease was activated as described for MMP-2 in Example II. Phage selections were performed with 2.5 mg/ml (56 nM) of active MMP-9. Following three rounds of exposure to MMP-9, individual phage clones were selected for sequencing. An alignment of the motifs revealed three groups of structurally distinct substrates (Table I). One group of substrates contain the motif with sequence Pro-X-X-$X_{Hy}$-Ser/Thr (SEQ ID NO:123). Further analysis shows that within this larger motif, Arg is favored at $P_2$ and Ser/Thr is favored at $P_1$. Other groups of substrates contained a Gly-Leu-Lys/Arg (SEQ ID NO:124) motif, a Arg-Arg-$X_{Hy}$-Leu (SEQ ID NO:125) motif, and a Arg-X-Leu motif. These last two sub-classes have not previously been described as a substrate motif for MMP-9. The ability of MMP-9 to hydrolyze each of the phage clones was assessed in a semi-quantitative manner using a modified ELISA as described in Example II. The position of scissile bonds within MMP-9 substrates was determined as in Example V.

Kinetic characterization of substrate hydrolysis by MMP-9

The Michaelis constant ($K_m$) and first-order rate constant of substrate peptide turnover ($k_{cat}$) were measured by incubating a range of each peptide with MMP-9. Peptide hydrolysis was measured by incorporation of fluorescamine onto newly formed amino-termini as previously described. From these measurements, $k_{cat}$ and $K_m$ were derived for each peptide using double-reciprocal plots of 1/[S] vs 1/$v_i$. Among the peptides, the $k_{cat}$ values ranged from 9 s$^{-1}$ to 703 s$^{-1}$, and $K_m$ values were generally in the high micromolar to low millimolar range.

Interestingly, the three peptides cleaved most efficiently by MMP-9 contained Arg at the $P_2$ position. We synthesized a mutant peptides (A11m1) that contains an Arg to Thr substitution at $P_1$ within the context of the sequence of the A11 peptide. Peptide A11m1 had a $k_{cat}/K_m$ twice that of the parent peptide, an effect resulting primarily from an increase in $k_{cat}$. This finding suggests that the substitution of Arg at $P_1$ lowers the transition state energy of the protease-substrate interaction. This observation also indicates that, within the Pro-X-X-$X_{Hy}$-Ser/Thr (SEQ ID NO:123) motif, Arg residues at $P_2$ and $P_1$ are favored for MMP-9.

In almost every case, the MMP-9 substrates selected from the phage library contain a hydrophobic residue at $P_{1'}$, a finding that is entirely consistent with the fact that MMPs are known to have a deep hydrophobic SI pocket. To assess the contribution of this hydrophobic residues to substrate binding and to substrate turnover, we synthesized another mutant peptide (A11m2) based on the sequence of peptide A11, but containing Ala, rather than Leu, at $P_{1'}$ (AC-SGKIPRTATA-NH2) (SEQ ID NO:126). This substitution had deleterious effects on both $k_{cat}$ and $K_m$, and reduced $k_{cat}/K_m$ ratio nearly 30-fold. These results are consistent with the idea that the S1' subsite of MMP-9 coordinates substrate binding and also influences the rate of hydrolysis. Even this mutant peptide had a measurable $k_{cat}/K_m$ ratio (2,000M$^{-1}$s$^{-1}$), indicating that efficient hydrolysis can be enacted by MMP-9 if the rest of the substrate sequence is optimal.

Kinetic characterization of substrate hydrolysis by MMP-7 and MMP-13

Since many of the selected substrates contained a motif similar to that described for other MMPs (P-X-X-$X_{Hy}$) (SEQ ID NO:127), we measured the degree to which MMP-7 and MMP-13 could cleave these MMP-9 substrates. These two MMPs were used for comparison because of their structural similarity to MMP-9 and because substrates for both proteases have been selected using a similar phage display approach. Most of the substrates we tested were cleaved more efficiently by MMP-9. The $k_{cat}/K_m$ ratios ranged from 2.6 to 47 fold higher for MMP-9 than for either MMP-7 or MMP-13 (Table II).

Modeling Substrate Interactions

Molecular modeling studies were conducted to help visualize how substrates might dock into the enzymatic cleft of MMP-9. Energy minimized models of MMP-9 were constructed and then docked with peptides A10 (AC-SGPLFYS-VTA-NH2) (SEQ ID NO:128) and C11 (Ac-SGRRLIHHTA-NH2) (SEQ ID NO:129).

Amino acids with long basic side chains at $P_2$ and $P_1$, such as Arg, are the defining features of some of the substrates. Although the presence of these residues at $P_2$ and $P_1$ is somewhat surprising, the energy-minimized models support the observation that these residues bind favorably. An Arg at $P_2$ is likely to interact with the backbone carbonyl moieties of His405, Gly408 and the side chain of Asp410, all of which contribute to the S2 subsite within MMP-9. These electrostatic interactions are predicted to contribute to favorable binding of this class of substrates. Many of the substrates also contain an Arg residue at $P_1$. The favorable interaction of Arg into the S1 subsite can be explained by the somewhat unusual nature of this subsite. It is essentially a hydrophobic binding surface that would be predicted to accommodate the hydrophobic side chains of amino acids such as Ala, Phe, and Tyr. However, the docking studies of peptides with Arg at $P_2$ show that the hydrophobic surface of the S2 subsite could also bind to the extended methylene group in the side chain of Arg. In addition, the hydrophobic channel of the S2 subsite contains the backbone carbonyl of Pro 180, which is likely to engage in electrostatic interaction with the basic side chain of Arg, stabilizing the interaction.

EXAMPLE IV

MT1-MMP Selective Substrate Polypeptides

Polypeptide substrates for Membrane type-Matrix Metalloproteinase 1(MT1-MMP) were identified using substrate phage display as described for MMP-2 and MMP-9. Synthetic peptides that are analogous to the phage sequences were used to quantitate the level of selectivity between MT1-MMP and MMP-9 (see Table II). In total these data demonstrate the selectivity of these polypeptides for MT1-MMP.

EXAMPLE V

Identification of Scissile Bonds

To identify the position of the scissile bond (the site of cleavage by the proteinase) in the identified hexamer polypeptides, representative polypeptides were synthesized. The position of the scissile bond within the polypeptides was determined by exposing representative polypeptides to proteinase, and then measuring the mass of the fragments that are produced using MALDI-TOF mass spectrometry. In particular, the metalloproteinase of interest (at approximately 23 nM) was incubated with 100 mM of each representative polypeptide independently, in 50 mM Tris, pH 7.5, 100 mM NaCl, 10 mM $CaCl_2$ for 2 hours at 37° C. and the masses of the cleavage products were determined using a Voyager DE-RP MALDI-TOF mass spectrometer (PerSeptive Biosystems, Framingham, Mass.). Following hydrolysis, the polypeptide samples were prepared according to methods known in the art (Karas, M. *Biochem. Soc. Trans.* 24:897-900 (1996), Landry et al., *Anal. Biochem.* 279:1-8 (2000), Vorm et al., *Anal. Chem.*, 66:3281-3287 (1994), Shevchenko et al., *Anal. Chem.*, 68:850-858 (1996)). The results are presented in Table V below. In each case the observed polypeptide fragments allowed the precise determination of the scissile bonds for each polypeptide shown in Table I.

TABLE V

Masses of Peptide Substrates Cleaved by MMP's

| Peptide ID | phage clone | | | | P3 | P2 | P1 | P1' | P2' | P3' | Masses of Observed Cleavage Products |
|---|---|---|---|---|---|---|---|---|---|---|---|
| *MMP-2 Substrates* | | | | | | | | | | | |
| 1 | B49 | | | | L | R | L | A | A | I | T | A | 728.73 |
| 2 | B74 | | | | E | S | L | A | Y | Y | T | A | 804.27 |
| 10 | C9 | | | | R | S | L | S | R | L | T | A | 790.29 |
| 11 | A34 | | | | N | R | Y | S | S | L | T | A | 812.41 |
| 12 | A13 | | | | G | A | V | S | W | L | L | T | 670.06 |
| 13 | B37 | | | | A | N | I | S | D | L | T | A | 729.03 |
| *MMP-9 substrate* | | | | | | | | | | | |
| 28 | C15 | S | G | K | G | P | R | Q | I | T | A | 771.05 |
| | | | | | | | | | | | | 793.02 |
| 29 | A11 | S | G | K | I | P | R | T | L | T | A | 799.82 |
| 30 | A6 | | | S | G | P | R | A | V | S | T | T | A | 529.36 |
| | | | | | | | | | | | | 551.33 |
| *MT1-MMP Substrates* | | | | | | | | | | | |
| 36 | A42 | | S | G | R | I | G | F | L | R | T | A | 680.8 |
| 37 | B175 | | S | G | R | A | M | H | M | Y | T | A | 700.4 |
| 38 | A176 | | S | G | R | S | E | N | I | R | T | A | 680.8 |
| 39 | B149 | S | G | A | R | Y | R | W | L | T | A | 938.51 |
| 40 | B96 | S | G | L | I | S | H | S | I | T | A | 744.99 |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from that spirit of the invention. Accordingly, the invention is limited only by the following claims.

We claim:

1. An isolated matrix metalloproteinase-2 (MMP-2) selective substrate polypeptide, comprising the amino acid sequence selected from the group consisting of SEQ ID NOS: 1-7 and 9, wherein said MMP-2 selective substrate polypeptide has 100 or fewer amino acids and can be hydrolyzed by MMP-2.

2. The isolated MMP-2 selective substrate of claim 1, wherein said MMP-2 selective substrate polypeptide has 40 or fewer amino acids.

3. The isolated MMP-2 selective substrate of claim 1, wherein said MMP-2 selective substrate polypeptide has 20 or fewer amino acids.

4. The isolated MMP-2 selective substrate of claim 1, wherein said MMP-2 selective substrate polypeptide has 10 or fewer amino acids.

5. The isolated MMP-2 selective substrate polypeptide of claim 1, wherein said amino acid sequence is SEQ ID NO:1.

6. The isolated MMP-2 selective substrate polypeptide of claim 1, wherein said amino acid sequence is SEQ ID NO:2.

7. The isolated MMP-2 selective substrate polypeptide of claim 1, wherein said amino acid sequence is SEQ ID NO:3.

8. The isolated MMP-2 selective substrate polypeptide of claim 1, wherein said amino acid sequence is SEQ ID NO:4.

9. The isolated MMP-2 selective substrate polypeptide of claim 1, wherein said amino acid sequence is SEQ ID NO:5.

10. The isolated MMP-2 selective substrate polypeptide of claim 1, wherein said amino acid sequence is SEQ ID NO:6.

11. The isolated MMP-2 selective substrate polypeptide of claim 1, wherein said amino acid sequence is SEQ ID NO:7.

12. The isolated MMP-2 selective substrate polypeptide of claim 1, wherein said amino acid sequence is SEQ ID NO:9.

13. An isolated matrix metalloproteinase-2 (MMP-2) selective substrate polypeptide, consisting of the amino acid sequence selected from the group consisting of SEQ ID NOS 1-9, wherein said MMP-2 selective substrate polypeptide can be hydrolyzed by MMP-2.

14. The isolated MMP-2 selective substrate polypeptide of claim 13, wherein said amino acid sequence is SEQ ID NO:1.

15. The isolated MMP-2 selective substrate polypeptide of claim 13, wherein said amino acid sequence is SEQ ID NO:2.

16. The isolated MMP-2 selective substrate polypeptide of claim 13, wherein said amino acid sequence is SEQ ID NO:3.

17. The isolated MMP-2 selective substrate polypeptide of claim 13, wherein said amino acid sequence is SEQ ID NO:4.

18. The isolated MMP-2 selective substrate polypeptide of claim 13, wherein said amino acid sequence is SEQ ID NO:5.

19. The isolated MMP-2 selective substrate polypeptide of claim 13, wherein said amino acid sequence is SEQ ID NO:6.

20. The isolated MMP-2 selective substrate polypeptide of claim 13, wherein said amino acid sequence is SEQ ID NO:7.

21. The isolated MMP-2 selective substrate polypeptide of claim 13, wherein said amino acid sequence is SEQ ID NO:8.

22. The isolated MMP-2 selective substrate polypeptide of claim 13, wherein said amino acid sequence is SEQ ID NO:9.

23. The isolated MMP-2 selective substrate polypeptide of claim 13, wherein said polypeptide is linked to a moiety.

24. The isolated MMP-2 selective substrate polypeptide of claim 23, wherein said moiety is a diagnostic agent.

25. The isolated MMP-2 selective substrate polypeptide of claim 24, wherein said diagnostic agent is a quenched fluorophore.

26. The isolated MMP-2 selective substrate polypeptide of claim 23, wherein said moiety is a therapeutic moiety.

27. The isolated MMP-2 selective substrate polypeptide of claim 26, wherein said therapeutic moiety is a chemotherapeutic agent.

28. The isolated MMP-2 selective substrate polypeptide of claim 26, wherein said therapeutic moiety is selected from the group consisting of an anti-angiogenic agent, a pro-angiogenic agent and an agent that promotes tissue repair.

29. A fusion protein comprising a polypeptide fused to a matrix metalloproteinase-2 (MMP-2) selective substrate polypeptide consisting of the amino acid sequence selected from the group consisting of SEQ ID NO: 1-9, wherein said MMP-2 selective substrate polypeptide can be hydrolyzed by MMP-2.

30. The fusion protein of claim 29, wherein said amino acid sequence is SEQ ID NO:1.

31. The fusion protein of claim 29, wherein said amino acid sequence is SEQ ID NO:2.

32. The fusion protein of claim 29, wherein said amino acid sequence is SEQ ID NO:3.

33. The fusion protein of claim 29, wherein said amino acid sequence is SEQ ID NO:4.

34. The fusion protein of claim 29, wherein said amino acid sequence is SEQ ID NO:5.

35. The fusion protein of claim 29, wherein said amino acid sequence is SEQ ID NO:6.

36. The fusion protein of claim 29, wherein said amino acid sequence is SEQ ID NO:7.

37. The fusion protein of claim 29, wherein said amino acid sequence is SEQ ID NO:8.

38. The fusion protein of claim 29, wherein said amino acid sequence is SEQ ID NO:9.

* * * * *

SEQUENCE LISTING

<160> NUMBER OF SEQ ID NOS: 129

<210> SEQ ID NO 1
<211> LENGTH: 8
<212> TYPE: PRT
<213> ORGANISM: Artificial Sequence

```
<220> FEATURE:
<223> OTHER INFORMATION: synthetic construct

<400> SEQUENCE: 1

Leu Arg Leu Ala Ala Ile Thr Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: synthetic construct

<400> SEQUENCE: 2

Glu Ser Leu Ala Tyr Tyr Thr Ala
 1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Pro Met Ile Ser Val Leu Thr Ala
 1               5

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Ser Leu His Ser Ile Ile Thr
 1               5

<210> SEQ ID NO 5
<211> LENGTH: 8
<212> TYPE: PRT
<213> ORGANISM: Artificial Sequence
<220> FEATURE:
<223> OTHER INFORMATION: synthetic construct

<400> SEQUENCE: 5

Ser Asp Ile Arg Met Leu Thr Ala
 1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct

<400> SEQUENCE: 6

Phe Asn Leu Tyr Asn Leu Thr Ala
 1               5

<210> SEQ ID NO 7
<211> LENGTH: 7
<212> TYPE: PRT
<213> ORGANISM: Artificial Sequence
<220> FEATURE:
```

<223> OTHER INFORMATION: synthetic construct

<400> SEQUENCE: 7

Tyr Leu Gln Val Leu Leu Thr
 1               5

<210> SEQ ID NO 8
<211> LENGTH: 6
<212> TYPE: PRT
<213> ORGANISM: Artificial Sequence
<220> FEATURE:
<223> OTHER INFORMATION: synthetic construct

<400> SEQUENCE: 8

Ile Val Asn Leu Tyr Pro
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9

Val Gly Leu Ile Ala Ile Thr Ala
 1               5

<210> SEQ ID NO 10
<211> LENGTH: 8
<212> TYPE: PRT
<213> ORGANISM: Artificial Sequence
<220> FEATURE:
<223> OTHER INFORMATION: synthetic construct

<400> SEQUENCE: 10

Arg Ser Leu Ser Arg Leu Thr Ala
 1               5

<210> SEQ ID NO 11
<211> LENGTH: 8
<212> TYPE: PRT
<213> ORGANISM: Artificial Sequence
<220> FEATURE:
<223> OTHER INFORMATION: synthetic construct

<400> SEQUENCE: 11

Asn Arg Tyr Ser Ser Leu Thr Ala
 1               5

<210> SEQ ID NO 12
<211> LENGTH: 8
<212> TYPE: PRT
<213> ORGANISM: Artificial Sequence
<220> FEATURE:
<223> OTHER INFORMATION: synthetic construct

<400> SEQUENCE: 12

Gly Ala Val Ser Trp Leu Leu Thr
 1               5

<210> SEQ ID NO 13
<211> LENGTH: 8
<212> TYPE: PRT
<213> ORGANISM: Artificial Sequence
<220> FEATURE:
<223> OTHER INFORMATION: synthetic construct

```
<400> SEQUENCE: 13

Ala Asn Ile Ser Asp Leu Thr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic construct

<400> SEQUENCE: 14

Trp Thr Ser Ser Trp Leu Thr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic construct

<400> SEQUENCE: 15

Thr Ile Leu Ser Leu Leu Thr Ala
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic construct

<400> SEQUENCE: 16

Phe Asn Ser Met Leu Lys Thr
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic construct

<400> SEQUENCE: 17

His Met His Lys Ala Leu Thr Ala
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic construct

<400> SEQUENCE: 18

Leu His Arg Arg Ile Asp Thr
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic construct
```

```
<400> SEQUENCE: 19

Met His Ser Arg Pro Pro Thr
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic construct

<400> SEQUENCE: 20

His Met His Lys Ala Leu Thr Ala
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic construct

<400> SEQUENCE: 21

Arg His Leu Gly Leu Gln Thr
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic construct

<400> SEQUENCE: 22

Leu His Lys Lys Val His Thr
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic construct

<400> SEQUENCE: 23

Ala His Ala Lys His Trp Thr
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct

<400> SEQUENCE: 24

Ala Lys Pro Arg Ala Leu Thr Ala
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic construct

<400> SEQUENCE: 25
```

```
Pro Tyr Val Ile Trp Leu
 1               5

<210> SEQ ID NO 26
<211> LENGTH: 8
<212> TYPE: PRT
<213> ORGANISM: Artificial Sequence
<220> FEATURE:
<223> OTHER INFORMATION: synthetic construct

<400> SEQUENCE: 26

Glu Tyr Glu His Met Arg Thr Ala
 1               5

<210> SEQ ID NO 27
<211> LENGTH: 8
<212> TYPE: PRT
<213> ORGANISM: Artificial Sequence
<220> FEATURE:
<223> OTHER INFORMATION: synthetic construct

<400> SEQUENCE: 27

Ile Tyr Leu Gly Trp Ala Thr Ala
 1               5

<210> SEQ ID NO 28
<211> LENGTH: 8
<212> TYPE: PRT
<213> ORGANISM: Artificial Sequence
<220> FEATURE:
<223> OTHER INFORMATION: synthetic construct

<400> SEQUENCE: 28

Lys Gly Pro Arg Gln Ile Thr Ala
 1               5

<210> SEQ ID NO 29
<211> LENGTH: 8
<212> TYPE: PRT
<213> ORGANISM: Artificial Sequence
<220> FEATURE:
<223> OTHER INFORMATION: synthetic construct

<400> SEQUENCE: 29

Lys Ile Pro Arg Thr Leu Thr Ala
 1               5

<210> SEQ ID NO 30
<211> LENGTH: 6
<212> TYPE: PRT
<213> ORGANISM: Artificial Sequence
<220> FEATURE:
<223> OTHER INFORMATION: synthetic construct

<400> SEQUENCE: 30

Pro Arg Ala Val Ser Thr
 1               5

<210> SEQ ID NO 31
<211> LENGTH: 6
<212> TYPE: PRT
<213> ORGANISM: Artificial Sequence
<220> FEATURE:
<223> OTHER INFORMATION: synthetic construct

<400> SEQUENCE: 31
```

```
Pro Arg Pro Leu Ser Gly
 1               5

<210> SEQ ID NO 32
<211> LENGTH: 8
<212> TYPE: PRT
<213> ORGANISM: Artificial Sequence
<220> FEATURE:
<223> OTHER INFORMATION: synthetic construct

<400> SEQUENCE: 32

Phe Arg Pro Arg Ser Ile Thr Ala
 1               5

<210> SEQ ID NO 33
<211> LENGTH: 6
<212> TYPE: PRT
<213> ORGANISM: Artificial Sequence
<220> FEATURE:
<223> OTHER INFORMATION: synthetic construct

<400> SEQUENCE: 33

Pro Arg Ser Ile Ser Asn
 1               5

<210> SEQ ID NO 34
<211> LENGTH: 8
<212> TYPE: PRT
<213> ORGANISM: Artificial Sequence
<220> FEATURE:
<223> OTHER INFORMATION: synthetic construct

<400> SEQUENCE: 34

Asn Pro Pro Arg Tyr Leu Thr Ala
 1               5

<210> SEQ ID NO 35
<211> LENGTH: 8
<212> TYPE: PRT
<213> ORGANISM: Artificial Sequence
<220> FEATURE:
<223> OTHER INFORMATION: synthetic construct

<400> SEQUENCE: 35

Ser Val Pro Arg His Phe Thr Ala
 1               5

<210> SEQ ID NO 36
<211> LENGTH: 7
<212> TYPE: PRT
<213> ORGANISM: Artificial Sequence
<220> FEATURE:
<223> OTHER INFORMATION: synthetic construct

<400> SEQUENCE: 36

Arg Ile Gly Phe Leu Arg Thr
 1               5

<210> SEQ ID NO 37
<211> LENGTH: 7
<212> TYPE: PRT
<213> ORGANISM: Artificial Sequence
<220> FEATURE:
<223> OTHER INFORMATION: synthetic construct

<400> SEQUENCE: 37

Arg Ala Met His Met Tyr Thr
```

-continued

<210> SEQ ID NO 38
<211> LENGTH: 7
<212> TYPE: PRT
<213> ORGANISM: Artificial Sequence
<220> FEATURE:
<223> OTHER INFORMATION: synthetic construct

<400> SEQUENCE: 38

Arg Ser Glu Asn Ile Arg Thr
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic construct

<400> SEQUENCE: 39

Ala Arg Tyr Arg Trp Leu Thr Ala
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic construct

<400> SEQUENCE: 40

Leu Ile Ser His Ser Ile Thr Ala
1               5

<210> SEQ ID NO 41
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(1)
<223> OTHER INFORMATION: Xaa = Ile or Leu
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
     Met, Tyr, Phe, or Trp)

<400> SEQUENCE: 41

Xaa Xaa Xaa Xaa
1

<210> SEQ ID NO 42
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(4)
<223> OTHER INFORMATION: Xaa = Any Amino Acid

```
<400> SEQUENCE: 42

Xaa Ser Xaa Leu
 1

<210> SEQ ID NO 43
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
      Met, Tyr, Phe, or Trp)

<400> SEQUENCE: 43

His Xaa Xaa Xaa
 1

<210> SEQ ID NO 44
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (3)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
      Met, Tyr, Phe or Trp)
<220> FEATURE:
<221> NAME/KEY: VARIANT
<222> LOCATION: (5)...(5)
<223> OTHER INFORMATION: Xaa = Ser or Thr

<400> SEQUENCE: 44

Pro Arg Xaa Xaa Xaa
 1               5

<210> SEQ ID NO 45
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(1)
<223> OTHER INFORMATION: Xaa = Ile or Leu
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
      Met, Tyr, Phe, or Trp)
<220> FEATURE:
<221> NAME/KEY: VARIANT
<222> LOCATION: (5)...(5)
<223> OTHER INFORMATION: Xaa = Thr, Leu, Ile or Tyr
<220> FEATURE:
<221> NAME/KEY: VARIANT
```

```
<222> LOCATION: (6)...(6)
<223> OTHER INFORMATION: Xaa = any amino acid

<400> SEQUENCE: 45

Xaa Xaa Xaa Xaa Xaa Xaa
 1               5

<210> SEQ ID NO 46
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(1)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic Amino acid (Leu, Ile, Val,
      Met, Tyr, Phe or Trp)
<220> FEATURE:
<221> NAME/KEY: VARIANT
<222> LOCATION: (5)...(5)
<223> OTHER INFORMATION: Xaa = Thr, Leu or Lys
<220> FEATURE:
<221> NAME/KEY: VARIANT
<222> LOCATION: (6)...(6)
<223> OTHER INFORMATION: Xaa = Any Amino Acid

<400> SEQUENCE: 46

Xaa Ser Xaa Xaa Xaa Xaa
 1               5

<210> SEQ ID NO 47
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
      Met, Tyr, Phe or Trp)
<220> FEATURE:
<221> NAME/KEY: VARIANT
<222> LOCATION: (5)...(5)
<223> OTHER INFORMATION: Xaa = Any Amino Acid
<220> FEATURE:
<221> NAME/KEY: VARIANT
<222> LOCATION: (6)...(6)
<223> OTHER INFORMATION: Xaa = Thr or Ala

<400> SEQUENCE: 47

His Xaa Xaa Xaa Xaa Xaa
 1               5

<210> SEQ ID NO 48
<211> LENGTH: 3
<212> TYPE: PRT
<213> ORGANISM: Artificial Sequence
<220> FEATURE:
<223> OTHER INFORMATION: synthetic construct
```

```
<400> SEQUENCE: 48

Ile Thr Ala
1

<210> SEQ ID NO 49
<211> LENGTH: 3
<212> TYPE: PRT
<213> ORGANISM: Artificial Sequence
<220> FEATURE:
<223> OTHER INFORMATION: synthetic construct

<400> SEQUENCE: 49

Tyr Thr Ala
1

<210> SEQ ID NO 50
<211> LENGTH: 3
<212> TYPE: PRT
<213> ORGANISM: Artificial Sequence
<220> FEATURE:
<223> OTHER INFORMATION: synthetic construct

<400> SEQUENCE: 50

Leu Thr Ala
1

<210> SEQ ID NO 51
<211> LENGTH: 3
<212> TYPE: PRT
<213> ORGANISM: Artificial Sequence
<220> FEATURE:
<223> OTHER INFORMATION: synthetic construct

<400> SEQUENCE: 51

Ile Ile Thr
1

<210> SEQ ID NO 52
<211> LENGTH: 3
<212> TYPE: PRT
<213> ORGANISM: Artificial Sequence
<220> FEATURE:
<223> OTHER INFORMATION: synthetic construct

<400> SEQUENCE: 52

Leu Leu Thr
1

<210> SEQ ID NO 53
<211> LENGTH: 3
<212> TYPE: PRT
<213> ORGANISM: Artificial Sequence
<220> FEATURE:
<223> OTHER INFORMATION: synthetic construct

<400> SEQUENCE: 53

Leu Tyr Pro
1

<210> SEQ ID NO 54
<211> LENGTH: 3
<212> TYPE: PRT
<213> ORGANISM: Artificial Sequence
<220> FEATURE:
<223> OTHER INFORMATION: synthetic construct
```

```
<400> SEQUENCE: 54

Leu Leu Thr
 1

<210> SEQ ID NO 55
<211> LENGTH: 3
<212> TYPE: PRT
<213> ORGANISM: Artificial Sequence
<220> FEATURE:
<223> OTHER INFORMATION: synthetic construct

<400> SEQUENCE: 55

Leu Lys Thr
 1

<210> SEQ ID NO 56
<211> LENGTH: 3
<212> TYPE: PRT
<213> ORGANISM: Artificial Sequence
<220> FEATURE:
<223> OTHER INFORMATION: synthetic construct

<400> SEQUENCE: 56

Ile Asp Thr
 1

<210> SEQ ID NO 57
<211> LENGTH: 3
<212> TYPE: PRT
<213> ORGANISM: Artificial Sequence
<220> FEATURE:
<223> OTHER INFORMATION: synthetic construct

<400> SEQUENCE: 57

Pro Pro Thr
 1

<210> SEQ ID NO 58
<211> LENGTH: 3
<212> TYPE: PRT
<213> ORGANISM: Artificial Sequence
<220> FEATURE:
<223> OTHER INFORMATION: synthetic construct

<400> SEQUENCE: 58

Leu Gln Thr
 1

<210> SEQ ID NO 59
<211> LENGTH: 3
<212> TYPE: PRT
<213> ORGANISM: Artificial Sequence
<220> FEATURE:
<223> OTHER INFORMATION: synthetic construct

<400> SEQUENCE: 59

Val His Thr
 1

<210> SEQ ID NO 60
<211> LENGTH: 3
<212> TYPE: PRT
<213> ORGANISM: Artificial Sequence
<220> FEATURE:
<223> OTHER INFORMATION: synthetic construct

<400> SEQUENCE: 60
```

His Trp Thr
1

<210> SEQ ID NO 61
<211> LENGTH: 3
<212> TYPE: PRT
<213> ORGANISM: Artificial Sequence
<220> FEATURE:
<223> OTHER INFORMATION: synthetic construct

<400> SEQUENCE: 61

Ile Trp Leu
1

<210> SEQ ID NO 62
<211> LENGTH: 3
<212> TYPE: PRT
<213> ORGANISM: Artificial Sequence
<220> FEATURE:
<223> OTHER INFORMATION: synthetic construct

<400> SEQUENCE: 62

Arg Thr Ala
1

<210> SEQ ID NO 63
<211> LENGTH: 3
<212> TYPE: PRT
<213> ORGANISM: Artificial Sequence
<220> FEATURE:
<223> OTHER INFORMATION: synthetic construct

<400> SEQUENCE: 63

Ala Thr Ala
1

<210> SEQ ID NO 64
<211> LENGTH: 3
<212> TYPE: PRT
<213> ORGANISM: Artificial Sequence
<220> FEATURE:
<223> OTHER INFORMATION: synthetic construct

<400> SEQUENCE: 64

Val Ser Thr
1

<210> SEQ ID NO 65
<211> LENGTH: 3
<212> TYPE: PRT
<213> ORGANISM: Artificial Sequence
<220> FEATURE:
<223> OTHER INFORMATION: synthetic construct

<400> SEQUENCE: 65

Leu Ser Gly
1

<210> SEQ ID NO 66
<211> LENGTH: 3
<212> TYPE: PRT
<213> ORGANISM: Artificial Sequence
<220> FEATURE:
<223> OTHER INFORMATION: synthetic construct

<400> SEQUENCE: 66

```
Ile Ser Asn
1

<210> SEQ ID NO 67
<211> LENGTH: 3
<212> TYPE: PRT
<213> ORGANISM: Artificial Sequence
<220> FEATURE:
<223> OTHER INFORMATION: synthetic construct

<400> SEQUENCE: 67

Phe Thr Ala
1

<210> SEQ ID NO 68
<211> LENGTH: 3
<212> TYPE: PRT
<213> ORGANISM: Artificial Sequence
<220> FEATURE:
<223> OTHER INFORMATION: synthetic construct

<400> SEQUENCE: 68

Leu Arg Thr
1

<210> SEQ ID NO 69
<211> LENGTH: 3
<212> TYPE: PRT
<213> ORGANISM: Artificial Sequence
<220> FEATURE:
<223> OTHER INFORMATION: synthetic construct

<400> SEQUENCE: 69

Met Tyr Thr
1

<210> SEQ ID NO 70
<211> LENGTH: 3
<212> TYPE: PRT
<213> ORGANISM: Artificial Sequence
<220> FEATURE:
<223> OTHER INFORMATION: synthetic construct

<400> SEQUENCE: 70

Ile Arg Thr
1

<210> SEQ ID NO 71
<211> LENGTH: 5
<212> TYPE: PRT
<213> ORGANISM: Artificial Sequence
<220> FEATURE:
<223> OTHER INFORMATION: synthetic construct

<400> SEQUENCE: 71

Leu Arg Leu Ala Ala
1               5

<210> SEQ ID NO 72
<211> LENGTH: 5
<212> TYPE: PRT
<213> ORGANISM: Artificial Sequence
<220> FEATURE:
<223> OTHER INFORMATION: synthetic construct

<400> SEQUENCE: 72

Glu Ser Leu Ala Tyr
```

-continued

```
1               5

<210> SEQ ID NO 73
<211> LENGTH: 5
<212> TYPE: PRT
<213> ORGANISM: Artificial Sequence
<220> FEATURE:
<223> OTHER INFORMATION: synthetic construct

<400> SEQUENCE: 73

Pro Met Ile Ser Val
1               5

<210> SEQ ID NO 74
<211> LENGTH: 4
<212> TYPE: PRT
<213> ORGANISM: Artificial Sequence
<220> FEATURE:
<223> OTHER INFORMATION: synthetic construct

<400> SEQUENCE: 74

Ser Leu His Ser
1

<210> SEQ ID NO 75
<211> LENGTH: 5
<212> TYPE: PRT
<213> ORGANISM: Artificial Sequence
<220> FEATURE:
<223> OTHER INFORMATION: synthetic construct

<400> SEQUENCE: 75

Ser Asp Ile Arg Met
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic construct

<400> SEQUENCE: 76

Phe Asn Leu Tyr Asn
1               5

<210> SEQ ID NO 77
<211> LENGTH: 4
<212> TYPE: PRT
<213> ORGANISM: Artificial Sequence
<220> FEATURE:
<223> OTHER INFORMATION: synthetic construct

<400> SEQUENCE: 77

Tyr Leu Gln Val
1

<210> SEQ ID NO 78
<211> LENGTH: 3
<212> TYPE: PRT
<213> ORGANISM: Artificial Sequence
<220> FEATURE:
<223> OTHER INFORMATION: synthetic construct

<400> SEQUENCE: 78

Ile Val Asn
1
```

```
<210> SEQ ID NO 79
<211> LENGTH: 5
<212> TYPE: PRT
<213> ORGANISM: Artificial Sequence
<220> FEATURE:
<223> OTHER INFORMATION: synthetic construct

<400> SEQUENCE: 79

Val Gly Leu Ile Ala
 1               5

<210> SEQ ID NO 80
<211> LENGTH: 5
<212> TYPE: PRT
<213> ORGANISM: Artificial Sequence
<220> FEATURE:
<223> OTHER INFORMATION: synthetic construct

<400> SEQUENCE: 80

Arg Ser Leu Ser Arg
 1               5

<210> SEQ ID NO 81
<211> LENGTH: 5
<212> TYPE: PRT
<213> ORGANISM: Artificial Sequence
<220> FEATURE:
<223> OTHER INFORMATION: synthetic construct

<400> SEQUENCE: 81

Asn Arg Tyr Ser Ser
 1               5

<210> SEQ ID NO 82
<211> LENGTH: 5
<212> TYPE: PRT
<213> ORGANISM: Artificial Sequence
<220> FEATURE:
<223> OTHER INFORMATION: synthetic construct

<400> SEQUENCE: 82

Gly Ala Val Ser Trp
 1               5

<210> SEQ ID NO 83
<211> LENGTH: 5
<212> TYPE: PRT
<213> ORGANISM: Artificial Sequence
<220> FEATURE:
<223> OTHER INFORMATION: synthetic construct

<400> SEQUENCE: 83

Ala Asn Ile Ser Asp
 1               5

<210> SEQ ID NO 84
<211> LENGTH: 5
<212> TYPE: PRT
<213> ORGANISM: Artificial Sequence
<220> FEATURE:
<223> OTHER INFORMATION: synthetic construct

<400> SEQUENCE: 84

Trp Thr Ser Ser Trp
 1               5
```

```
<210> SEQ ID NO 85
<211> LENGTH: 5
<212> TYPE: PRT
<213> ORGANISM: Artificial Sequence
<220> FEATURE:
<223> OTHER INFORMATION: synthetic construct

<400> SEQUENCE: 85

Thr Ile Leu Ser Leu
 1               5

<210> SEQ ID NO 86
<211> LENGTH: 4
<212> TYPE: PRT
<213> ORGANISM: Artificial Sequence
<220> FEATURE:
<223> OTHER INFORMATION: synthetic construct

<400> SEQUENCE: 86

Phe Asn Ser Met
 1

<210> SEQ ID NO 87
<211> LENGTH: 5
<212> TYPE: PRT
<213> ORGANISM: Artificial Sequence
<220> FEATURE:
<223> OTHER INFORMATION: synthetic construct

<400> SEQUENCE: 87

His Met His Lys Ala
 1               5

<210> SEQ ID NO 88
<211> LENGTH: 4
<212> TYPE: PRT
<213> ORGANISM: Artificial Sequence
<220> FEATURE:
<223> OTHER INFORMATION: synthetic construct

<400> SEQUENCE: 88

Leu His Arg Arg
 1

<210> SEQ ID NO 89
<211> LENGTH: 4
<212> TYPE: PRT
<213> ORGANISM: Artificial Sequence
<220> FEATURE:
<223> OTHER INFORMATION: synthetic construct

<400> SEQUENCE: 89

Met His Ser Arg
 1

<210> SEQ ID NO 90
<211> LENGTH: 5
<212> TYPE: PRT
<213> ORGANISM: Artificial Sequence
<220> FEATURE:
<223> OTHER INFORMATION: synthetic construct

<400> SEQUENCE: 90

His Met His Lys Ala
 1               5
```

```
<210> SEQ ID NO 91
<211> LENGTH: 4
<212> TYPE: PRT
<213> ORGANISM: Artificial Sequence
<220> FEATURE:
<223> OTHER INFORMATION: synthetic construct

<400> SEQUENCE: 91

Arg His Leu Gly
 1

<210> SEQ ID NO 92
<211> LENGTH: 4
<212> TYPE: PRT
<213> ORGANISM: Artificial Sequence
<220> FEATURE:
<223> OTHER INFORMATION: synthetic construct

<400> SEQUENCE: 92

Leu His Lys Lys
 1

<210> SEQ ID NO 93
<211> LENGTH: 4
<212> TYPE: PRT
<213> ORGANISM: Artificial Sequence
<220> FEATURE:
<223> OTHER INFORMATION: synthetic construct

<400> SEQUENCE: 93

Ala His Ala Lys
 1

<210> SEQ ID NO 94
<211> LENGTH: 5
<212> TYPE: PRT
<213> ORGANISM: Artificial Sequence
<220> FEATURE:
<223> OTHER INFORMATION: synthetic construct

<400> SEQUENCE: 94

Ala Lys Pro Arg Ala
 1               5

<210> SEQ ID NO 95
<211> LENGTH: 3
<212> TYPE: PRT
<213> ORGANISM: Artificial Sequence
<220> FEATURE:
<223> OTHER INFORMATION: synthetic construct

<400> SEQUENCE: 95

Pro Tyr Val
 1

<210> SEQ ID NO 96
<211> LENGTH: 5
<212> TYPE: PRT
<213> ORGANISM: Artificial Sequence
<220> FEATURE:
<223> OTHER INFORMATION: synthetic construct

<400> SEQUENCE: 96

Glu Tyr Glu His Met
 1               5

<210> SEQ ID NO 97
```

```
<211> LENGTH: 5
<212> TYPE: PRT
<213> ORGANISM: Artificial Sequence
<220> FEATURE:
<223> OTHER INFORMATION: synthetic construct

<400> SEQUENCE: 97

Ile Tyr Leu Gly Trp
 1               5

<210> SEQ ID NO 98
<211> LENGTH: 5
<212> TYPE: PRT
<213> ORGANISM: Artificial Sequence
<220> FEATURE:
<223> OTHER INFORMATION: synthetic construct

<400> SEQUENCE: 98

Lys Gly Pro Arg Gln
 1               5

<210> SEQ ID NO 99
<211> LENGTH: 5
<212> TYPE: PRT
<213> ORGANISM: Artificial Sequence
<220> FEATURE:
<223> OTHER INFORMATION: synthetic construct

<400> SEQUENCE: 99

Lys Ile Pro Arg Thr
 1               5

<210> SEQ ID NO 100
<211> LENGTH: 3
<212> TYPE: PRT
<213> ORGANISM: Artificial Sequence
<220> FEATURE:
<223> OTHER INFORMATION: synthetic construct

<400> SEQUENCE: 100

Pro Arg Ala
 1

<210> SEQ ID NO 101
<211> LENGTH: 3
<212> TYPE: PRT
<213> ORGANISM: Artificial Sequence
<220> FEATURE:
<223> OTHER INFORMATION: synthetic construct

<400> SEQUENCE: 101

Pro Arg Pro
 1

<210> SEQ ID NO 102
<211> LENGTH: 5
<212> TYPE: PRT
<213> ORGANISM: Artificial Sequence
<220> FEATURE:
<223> OTHER INFORMATION: synthetic construct

<400> SEQUENCE: 102

Phe Arg Pro Arg Ser
 1               5

<210> SEQ ID NO 103
<211> LENGTH: 3
```

```
<212> TYPE: PRT
<213> ORGANISM: Artificial Sequence
<220> FEATURE:
<223> OTHER INFORMATION: synthetic construct

<400> SEQUENCE: 103

Pro Arg Ser
 1

<210> SEQ ID NO 104
<211> LENGTH: 5
<212> TYPE: PRT
<213> ORGANISM: Artificial Sequence
<220> FEATURE:
<223> OTHER INFORMATION: synthetic construct

<400> SEQUENCE: 104

Asn Pro Pro Arg Tyr
 1               5

<210> SEQ ID NO 105
<211> LENGTH: 5
<212> TYPE: PRT
<213> ORGANISM: Artificial Sequence
<220> FEATURE:
<223> OTHER INFORMATION: synthetic construct

<400> SEQUENCE: 105

Ser Val Pro Arg His
 1               5

<210> SEQ ID NO 106
<211> LENGTH: 4
<212> TYPE: PRT
<213> ORGANISM: Artificial Sequence
<220> FEATURE:
<223> OTHER INFORMATION: synthetic construct

<400> SEQUENCE: 106

Arg Ile Gly Phe
 1

<210> SEQ ID NO 107
<211> LENGTH: 4
<212> TYPE: PRT
<213> ORGANISM: Artificial Sequence
<220> FEATURE:
<223> OTHER INFORMATION: synthetic construct

<400> SEQUENCE: 107

Arg Ala Met His
 1

<210> SEQ ID NO 108
<211> LENGTH: 4
<212> TYPE: PRT
<213> ORGANISM: Artificial Sequence
<220> FEATURE:
<223> OTHER INFORMATION: synthetic construct

<400> SEQUENCE: 108

Arg Ser Glu Asn
 1

<210> SEQ ID NO 109
<211> LENGTH: 5
<212> TYPE: PRT
```

<210> SEQ ID NO 109
<211> LENGTH: 5
<212> TYPE: PRT
<213> ORGANISM: Artificial Sequence
<220> FEATURE:
<223> OTHER INFORMATION: synthetic construct

<400> SEQUENCE: 109

Ala Arg Tyr Arg Trp
 1               5

<210> SEQ ID NO 110
<211> LENGTH: 5
<212> TYPE: PRT
<213> ORGANISM: Artificial Sequence
<220> FEATURE:
<223> OTHER INFORMATION: synthetic construct

<400> SEQUENCE: 110

Leu Ile Ser His Ser
 1               5

<210> SEQ ID NO 111
<211> LENGTH: 34
<212> TYPE: DNA
<213> ORGANISM: Artificial Sequence
<220> FEATURE:
<223> OTHER INFORMATION: synthetic construct

<400> SEQUENCE: 111
ccgggtttgt cgtcgtcgtc tttgtagtcg gtac                           34

<210> SEQ ID NO 112
<211> LENGTH: 26
<212> TYPE: DNA
<213> ORGANISM: Artificial Sequence
<220> FEATURE:
<223> OTHER INFORMATION: synthetic construct

<400> SEQUENCE: 112
cgactacaaa gacgacgacg acaaac                                    26

<210> SEQ ID NO 113
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(75)
<223> OTHER INFORMATION: n = A,T,C or G

<400> SEQUENCE: 113
ggggaggccg acgtggccgt catcaggcgg ctcaggcnnk nnknnknnkn nknnkacggc    60
ctctggggcc gaaac                                                75

<210> SEQ ID NO 114
<211> LENGTH: 5
<212> TYPE: DNA
<213> ORGANISM: Artificial Sequence
<220> FEATURE:
<223> OTHER INFORMATION: synthetic construct

<400> SEQUENCE: 114 sggsg                                                            5

<210> SEQ ID NO 115
<211> LENGTH: 25

<212> TYPE: DNA
<213> ORGANISM: Artificial Sequence
<220> FEATURE:
<223> OTHER INFORMATION: synthetic construct

<400> SEQUENCE: 115
aatttctagt ttcggcccca gaggc                                    25

<210> SEQ ID NO 116
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: (0)...(0)
<220> FEATURE:
<221> NAME/KEY: VARIANT
<222> LOCATION: (2)...(2)
<223> OTHER INFORMATION: Xaa = L-cyclohexylalanine
<220> FEATURE:
<221> NAME/KEY: VARIANT
<222> LOCATION: (4)...(4)
<223> OTHER INFORMATION: Xaa = L-norvaline
<220> FEATURE:
<221> NAME/KEY: VARIANT
<222> LOCATION: (7)...(7)
<223> OTHER INFORMATION: Xaa = 3-(2,4-dinitrophenyl)-L-2,3-
      diaminopropionyl

<400> SEQUENCE: 116

Pro Xaa Gly Xaa His Ala Xaa
 1               5

<210> SEQ ID NO 117
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: (0)...(0)
<220> FEATURE:
<221> NAME/KEY: VARIANT
<222> LOCATION: (5)...(5)
<223> OTHER INFORMATION: Xaa = 3-(2,4-dinitrophenyl)-L-2,3-
      diaminopropionyl

<400> SEQUENCE: 117

Pro Leu Gly Leu Xaa Ala Arg
 1               5

<210> SEQ ID NO 118
<211> LENGTH: 6
<212> TYPE: PRT
<213> ORGANISM: Artificial Sequence
<220> FEATURE:
<223> OTHER INFORMATION: synthetic construct

<400> SEQUENCE: 118

Ser Ile Ser Ser Leu Trp
 1               5

<210> SEQ ID NO 119
<211> LENGTH: 4
<212> TYPE: PRT
<213> ORGANISM: Artificial Sequence
<220> FEATURE:
<223> OTHER INFORMATION: synthetic construct

```
<220> FEATURE:
<221> NAME/KEY: VARIANT
<222> LOCATION: (1)...(1)
<223> OTHER INFORMATION: Xaa = Hydrophobic Amino acid (Leu, Ile, Val,
      Met, Tyr, Phe or Trp)
<220> FEATURE:
<221> NAME/KEY: VARIANT
<222> LOCATION: (3)...(3)
<223> OTHER INFORMATION: Xaa = Any Amino Acid

<400> SEQUENCE: 119

Xaa Ser Xaa Leu
 1

<210> SEQ ID NO 120
<211> LENGTH: 4
<212> TYPE: PRT
<213> ORGANISM: Artificial Sequence
<220> FEATURE:
<223> OTHER INFORMATION: synthetic construct

<400> SEQUENCE: 120

Lys Ser Glu Leu
 1

<210> SEQ ID NO 121
<211> LENGTH: 6
<212> TYPE: PRT
<213> ORGANISM: Artificial Sequence
<220> FEATURE:
<223> OTHER INFORMATION: synthetic construct

<400> SEQUENCE: 121

Tyr Ile Ser Asp Leu Leu
 1               5

<210> SEQ ID NO 122
<211> LENGTH: 9
<212> TYPE: PRT
<213> ORGANISM: Artificial Sequence
<220> FEATURE:
<223> OTHER INFORMATION: synthetic construct

<400> SEQUENCE: 122

Asp Asp Tyr Lys Ser Glu Leu Arg Glu
 1               5

<210> SEQ ID NO 123
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic amino acid (Leu, Ile, Val,
      Met, Tyr, Phe or Trp)
<220> FEATURE:
<221> NAME/KEY: VARIANT
<222> LOCATION: (5)...(5)
<223> OTHER INFORMATION: Xaa = Ser or Thr

<400> SEQUENCE: 123

Pro Xaa Xaa Xaa Xaa
 1               5
```

```
<210> SEQ ID NO 124
<211> LENGTH: 3
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (3)...(3)
<223> OTHER INFORMATION: Xaa = Lys or Arg

<400> SEQUENCE: 124

Gly Leu Xaa
1

<210> SEQ ID NO 125
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (3)...(3)
<223> OTHER INFORMATION: Xaa = Hydrophobic Amino acid (Leu, Ile, Val,
      Met, Tyr, Phe, or Trp)

<400> SEQUENCE: 125

Arg Arg Xaa Leu
1

<210> SEQ ID NO 126
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: ACETYLATION
<222> LOCATION: (1)...(0)
<220> FEATURE:
<221> NAME/KEY: AMIDATION
<222> LOCATION: (10)...(0)

<400> SEQUENCE: 126

Ser Gly Lys Ile Pro Arg Thr Ala Thr Ala
1               5                   10

<210> SEQ ID NO 127
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Hydrophobic Amino acid (Leu, Ile, Val,
      Met, Tyr, Phe or Trp)

<400> SEQUENCE: 127

Pro Xaa Xaa Xaa
1

<210> SEQ ID NO 128
```

```
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: ACETYLATION
<222> LOCATION: (1)...(0)
<220> FEATURE:
<221> NAME/KEY: AMIDATION
<222> LOCATION: (10)...(0)

<400> SEQUENCE: 128

Ser Gly Pro Leu Phe Tyr Ser Val Thr Ala
 1               5                  10

<210> SEQ ID NO 129
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: ACETYLATION
<222> LOCATION: (1)...(0)
<220> FEATURE:
<221> NAME/KEY: AMIDATION
<222> LOCATION: (10)...(0)

<400> SEQUENCE: 129

Ser Gly Arg Arg Leu Ile His His Thr Ala
 1               5                  10
```